US008017627B2

(12) United States Patent  (10) Patent No.: US 8,017,627 B2
Grarup et al.  (45) Date of Patent: Sep. 13, 2011

(54) FENTANYL COMPOSITION FOR NASAL ADMINISTRATION

(75) Inventors: Jesper Grarup, Roskilde (DK); Hanne Wulf Nielsen, Svenborg (DK)

(73) Assignee: Nycomed Danmark APS, Roskilde (DK)

( * ) Notice: Subject to any disclaimer, the term of this patent is extended or adjusted under 35 U.S.C. 154(b) by 803 days.

(21) Appl. No.: 10/343,449

(22) PCT Filed: Jul. 31, 2001

(86) PCT No.: PCT/DK01/00521
§ 371 (c)(1),
(2), (4) Date: Jul. 14, 2003

(87) PCT Pub. No.: WO02/09707
PCT Pub. Date: Feb. 7, 2002

(65) Prior Publication Data
US 2004/0034059 A1  Feb. 19, 2004

(30) Foreign Application Priority Data
Jul. 31, 2000 (DK) .................................. 2000 01154

(51) Int. Cl.
*A61K 31/445* (2006.01)
*A61K 9/12* (2006.01)
(52) U.S. Cl. ........... 514/317; 514/316; 514/329; 424/44
(58) Field of Classification Search .................. 514/282, 514/316, 329; 424/267
See application file for complete search history.

(56) References Cited

U.S. PATENT DOCUMENTS

| | | | |
|---|---|---|---|
| 4,464,378 A | 8/1984 | Hussain | |
| 4,486,423 A * | 12/1984 | Kenyhercz | 514/329 |
| 4,588,580 A | 5/1986 | Gale et al. | |
| 4,806,341 A | 2/1989 | Chien et al. | |
| 4,885,305 A | 12/1989 | Kiechel et al. | |
| 4,916,142 A | 4/1990 | Bagley et al. | |
| 5,019,583 A | 5/1991 | Feldman et al. | |
| 5,028,616 A | 7/1991 | Desai et al. | |
| 5,098,915 A | 3/1992 | Desai et al. | |
| 5,466,700 A | 11/1995 | Batenhorst et al. | |
| 5,543,434 A | 8/1996 | Weg | |
| 5,693,608 A | 12/1997 | Bechgaard et al. | |
| 5,735,263 A | 4/1998 | Rubsamen et al. | |
| 5,910,301 A | 6/1999 | Rowe et al. | |
| 5,958,379 A | 9/1999 | Regenold et al. | |
| 6,017,963 A * | 1/2000 | Alfonso et al. | 514/646 |
| 6,066,650 A | 5/2000 | Biller et al. | |
| 6,143,278 A | 11/2000 | Elkhoury | |
| 6,310,072 B1 | 10/2001 | Smith et al. | |
| 6,541,021 B1 * | 4/2003 | Johnson et al. | 424/422 |
| 6,608,073 B1 | 8/2003 | Hussain et al. | |
| 6,645,980 B1 | 11/2003 | Cuny et al. | |
| 6,660,715 B2 | 12/2003 | Klibanov | |
| 6,663,883 B1 | 12/2003 | Akiyama et al. | |
| RE38,407 E | 1/2004 | Mezel et al. | |
| 6,680,071 B1 | 1/2004 | Johnson et al. | |
| 6,689,373 B2 * | 2/2004 | Johnson et al. | 424/422 |
| 6,787,149 B1 | 9/2004 | El Khoury et al. | |
| 6,939,876 B2 | 9/2005 | Dewey et al. | |
| 6,946,150 B2 | 9/2005 | Whittle | |
| 6,955,824 B1 | 10/2005 | Hallworth | |
| 7,049,326 B2 | 5/2006 | Erhardt | |
| 7,074,803 B2 | 7/2006 | Litmanovitz et al. | |
| 7,090,866 B2 | 8/2006 | Johnson et al. | |
| 7,129,228 B2 | 10/2006 | Cuny et al. | |
| 7,201,920 B2 | 4/2007 | Kumar et al. | |
| 2002/0106407 A1 | 8/2002 | Coleman et al. | |
| 2003/0077300 A1 | 4/2003 | Wermeling | |
| 2003/0091512 A1 | 5/2003 | Adjei et al. | |
| 2003/0190290 A1 | 10/2003 | Ross | |
| 2004/0034059 A1 | 2/2004 | Grarup et al. | |
| 2004/0102476 A1 | 5/2004 | Chan et al. | |
| 2004/0115133 A1 | 6/2004 | Wermeling | |
| 2004/0166067 A1 | 8/2004 | Watts et al. | |
| 2004/0180080 A1 | 9/2004 | Furusawa et al. | |
| 2005/0137229 A1 | 6/2005 | Fish et al. | |
| 2006/0062812 A1 | 3/2006 | Ross et al. | |
| 2006/0110333 A1 | 5/2006 | Yanagawa | |
| 2007/0014820 A1 | 1/2007 | Litmanovitz et al. | |
| 2007/0092535 A1 | 4/2007 | Watts et al. | |
| 2007/0110677 A1 | 5/2007 | Watts et al. | |
| 2007/0261695 A1 | 11/2007 | Kottayil et al. | |

FOREIGN PATENT DOCUMENTS

AU  B0 565177  7/1987

(Continued)

OTHER PUBLICATIONS

Zandsberg et al. Nonconventional drug administration in anesthesia. New Drugs in Anesthesia: Part II Anesthesiology Clinics of North America vol. 12, No. 1 Mar. 1994. pp. 17-38.*
Drug Facts and Comparisons, 1997 Edition. pp. 1320.*
Younge et al., *Emergency Medicine*, vol. 11, pp. 90-94 (1999).
Striebel et al., *Anaesthesia*, vol. 48, pp. 753-757 (1993).
Streisand, James B. et al., "Buccal Absorption of Fentanyl Is pH-Dependent in Dogs", *Anesthesiology*, vol. 82, No. 3, 759-764, Mar. 1995.
Sebel, P.S. et al., "Transdermal Absorption of Fentanyl and Sufentanil in Man", *Eur J Clin Pharmacol* (1987)32: 529-531, 1987.
Hans Walter Striebel et al., "Postoperative Pain Management by Intranasal Demand-adapted Fentanyl Titration", Anesthesiology, vol. 77, pp. 281-285 (1992).
H.W. Striebel et al., "Pharmakokinetische Studie zur intranasalen Gabe von Fentanyl", Der Schmerz, vol. 7, pp. 122-125 (1993).

(Continued)

*Primary Examiner* — Jennifer M Kim
(74) *Attorney, Agent, or Firm* — Wenderoth, Lind & Ponack, L.L.P.

(57) ABSTRACT

The treatment of acute pain with a sufficient dosage by intranasal administration of fentanyl results in a time to onset of action comparable to intravenous administration and a significantly faster onset of action than nasal titration of fentanyl. The nasal administration of a sufficient amount of fentanyl to obtain pain relief has lower maximum plasma concentrations comparable to intravenous administration and results in lower rates of adverse events like respiratory depression, nausea and vomiting. Compositions for use in the method are also disclosed.

24 Claims, 13 Drawing Sheets

FOREIGN PATENT DOCUMENTS

Figure 1:
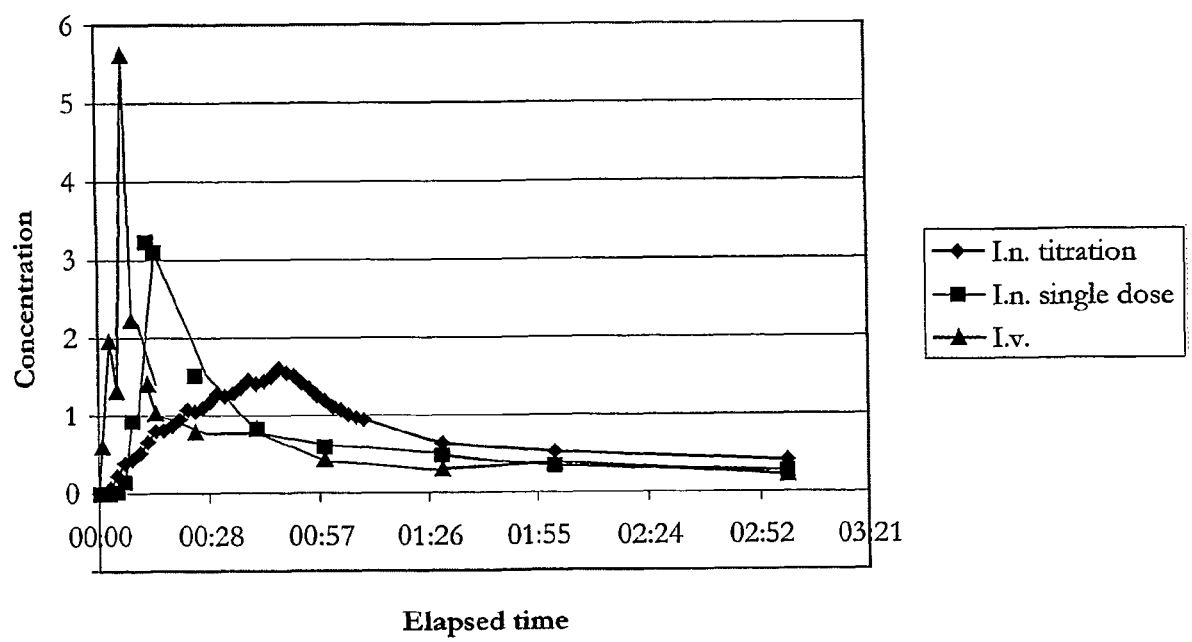

| | | |
|---|---|---|
| AU | C0 565177 | 7/1987 |
| EP | 0 255 485 A | 2/1988 |
| WO | 90/07333 | 7/1990 |
| WO | 91 03271 A | 3/1991 |
| WO | 94/10987 | 5/1994 |
| WO | 96/39222 | 12/1996 |
| WO | 96/39223 | 12/1996 |
| WO | 96/39224 | 12/1996 |
| WO | 98/34596 | 8/1998 |
| WO | 98/47535 | 10/1998 |
| WO | 00/16750 | 3/2000 |
| WO | 00/16751 | 3/2000 |
| WO | 00/24373 | 5/2000 |
| WO | 00/47203 | 8/2000 |
| WO | 01/97780 | 12/2001 |
| WO | 02/00195 | 1/2002 |
| WO | 02/09707 | 2/2002 |
| WO | 02/051380 | 7/2002 |
| WO | 2004/062561 | 7/2004 |
| WO | 2007/007059 | 1/2007 |
| WO | 2007/087431 | 8/2007 |
| WO | 2009/017837 | 2/2009 |
| WO | 2009/047779 | 4/2009 |
| WO | 2009/070829 | 6/2009 |

OTHER PUBLICATIONS

R. Scwagmeier, et al., "Patientenakzeptanz gegenüber der patientenköntrollierten intranasalen Analgesie (PCINA)", Anaesthesist, vol. 45, pp. 231-234 (1996).
G. O'Neil et al., "Preliminary Clinical Use of a Patient-Controlled Intranasil Analgesia (PCINA) Device", Anaesthesia and Intensive Care, vol. 25. No. 4, pp. 408-412 (1997).
F. Camu et al., "Postoperative Analgesic Effects of Three Demand-Dose Sizes of Fentanyl Administered by Patient-Controlled Analgesia", Anesth. Analg., vol. 87, pp. 890-895 (1998).
M. H. Worsley et al., "Inhaled Fentanyl as a Method of Analgesia", Anaesthesia, vol. 45, pp. 449-451 (1990).
H. Walter Striebel et al., "Patient-Controlled Intranasal Analgesia (PCINA) for the Management of Postoperative Pain: a Pilot Study", Journal of Clinical Anesthesia, vol. 18, pp. 4-8 (1996).
A. Brusset et al., "Comparative Pharmacokinetic Study of Fentanyl and Sufentanil After Single High-Bolus Doses", Clin Drug Invest, vol. 8(5), pp. 377-389 (1999).
Samir D. Roy et al., "Solubility Behavior of Narcotic Analgesics in Aqueous Media: Solubilities and Dissociation Constants of Morphine, Fentanyl, and Sufentanil", Pharmaceutical Research, vol. 6, No. 2, pp. 147-151 (1989).
Philip W. H. Peng, et al., "A Review of the Use of Fentanyl Analgesia in the Management of Acute Pain in Adults", Anesthesiology, vol. 90, No. 2, pp. 576-579 (1999).
James F. Cleary, "Pharmacokinetic and Pharmcodynamic Issues in the Treatment of Breakthrough Pain". Seminars in Oncology, vol. 24., No. 5 Suppl 16, pp. 516-13 to 516-19 (1997).
H. W. Stribel et al., "Die intranasale Opioidgabe zur Therapie von Schmerzen—ein neuer Applikationsweg", Aneästhesiologie & Intensivmedizin, vol. 3(37), pp. 128-134 (1996).
"Martindale the extra pharmacopoeia" Royal Pharmaceutical Society, London, XP002154769, pp. 43-46 (1996).
G. Zeppetella, An assessment of the safety, efficacy, and acceptability of intranasal fentanyl citrate in the management of cancer related breakthrough pain: a pilot study. J. Pain and Symptom Management, 20(4), 253-258 (2000).
Jaffe et al., Psychopharmacology, 99, 289-293 (1989).
G. Zeppetella, Nebulized and intranasal fentanyl in the management of cancer-related breakthrough pain. Palliat. Med., 14(1), 57-58 (2000).
S. Ahmedzai et al., Nebulized Drugs in Palliative Care, Thorax, 52 (Supp.2), S75-S77 (1997).
L.M. Joly et al., "Patient-Controlled Intranasal Analgesia", Anesth Analg. 1997; 85:463-466.
Hans W. Striebel, et al. "Patient-Controlled Intranasal Analgesia: A Method for Noninvasive Postoperative Pain Management", Anesth Analg 1996; 83:548-51.
Walter Streibel et al., "Pharmacokinetics of intranasal fentanyl", BR J Anaesth, 1993, 70 (suppl), A.208.
Walter Streibel et al., "Intranasal Fentanyl for Postoperative Pain Management in an Unselected Population", BR J Anaesth, 1993, 70 (suppl), A.209.
Walter Hermens et al., "The In Vitro Effect of Morphine, Fentanyl and Sufentanil on Ciliary Beat Frequency of Human Nasal Epithelial Tissue", Acta Pharm Technol, 33 (2), pp. 88-90, 1987.
Kadriye Türkay Kahveci et al., "Cocuklarda Premedikasyonda Intranazal Midazolam, Ketamin, Alfentanil, Fentanil, Etkinliginin Karsilastirilmasi", Türk Anest Rean Mecmuasi, 25: 229-304, 1987.
Fiona Rally, "Intranasal opiates: old route for new drugs", Can J. Anaesth 46, pp. 491-493, 1989.
Walter Streibel et al., "Intranasal Fentanyl for breakthrough cancer paint or incident pain", BR J Anaesth, 1993, 70 (suppl), A.210.
Hayri Ozbek et al., "Comparison of the Effects of Intranasal and Intravenous Fentanyl Administration on Postoperative Pain Relief", Journal of Turkish Anesthesiology and Recovery Association, 25, pp. 467-470, 1997.
G. Isik et al., "The Effects of Intranasal Fentanyl and Alfentanyl in Postoperative Pain Relief", Agri. Dergisi, Cilt: 7, 3, pp. 18-22, 1995.
Jeffrey L. Galinkin et al., "Use of Intranasal Fentanyl in Children Undergoing Myringotomy and Tube Placement during Halothane and Sevoflurane Anesthesia", Anesthesiology, vol. 93, No. 6, pp. 1378-1383, Dec. 2000.
Julia C. Finkel et al., "The Effect of Intranasal Fentanyl on the Emergence Characteristics After Sevoflurane Anesthesia in Children Undergoing Surgery for Bilateral Myringotomy Tube Placement", Anesth. Analg., 92, pp. 1164-1168, 2001.
Jeffrey L. Gaunkin et al., "Blood Levels of Fentanyl After Intranasal Administration in Children Undergoing Bilateral Myringotomy and Tube Placement (BMT)", ASA Abstracts, Anesthesiology, vol. 91, No. 3A, A1279, Sep. 1999.
"Fentanyl 25-ug/0.1-mL Nasal Spray", International Journal of Pharmaceutical Compounding, vol. 4, No. 1, p. 57, Jan./Feb. 2000.
The Merck Index, An Encyclopedia of Chemicals, Drugs, and Biologicals, Twelfth Edition, pp. 679-680, 1996.
Susanne Toussaint et al., "Patient-controlled intranasal analgesia: effective alternative to intravenous PCA for postoperative pain relief", Canadian Journal of Anesthesia, vol. 47, No. 1, pp. 299-302, Jan. 2000.
Hans Walter Striebel et al., "Non-invasive methods for PCA in pain management", Acute Pain, vol. (2), No. 1, pp. 36-40, Mar. 1999.
H.W. Striebel et al., "Patient-controlled Intranasal Analesia (PCINA) for Postoperative Pain Management—A Pilot Study", Anaesthesist (Springer), vol. 43, supplement 1, abstract FV34.6, p. 215, (1994).
T. Kondo et al., "Effects of Cyclodextrins on Nasal Absorption and Analgesic Activity of Opioids in Rats", Proceedings of the Eighth International Symposium on Cyclodextrins, Budapest, Hungary, pp. 387-390, Mar.-Apr. 1996.
Wang Xiaobin et al., "Observation of the Postoperative Analgesic Effects of Small-dose Fentanyl Nasal Spray", Journal of Luzhou Medical College, vol. 21, No. 2, pp. 149-150, 1998.
Bao Ting-Li, "Clinical Observation of Analgesia using Fentanyl and Ketamine Nasal Spray in Abortion", Chinese Community Doctors, pp. 35-36, 2003.
Third Party Observations (in English) Under Article 115(1) EPC received by the EPO on Apr. 3, 2007 in connection with the European application corresponding to the present application U.S. application.
Third Party Observations (in English) Under Article 115(1) EPC received by the EPO on Nov. 1, 2007 in connection with the European application corresponding to the present U.S. application.
Thomas Pasch et al., "Propofol Anaesthesia with Spontaneous Breathing for Extra-Corporeal Shock Wave Lithotripsy", Br. J. Anaesth., vol. 70, Suppl. 1, p. 79, A.153, 1993.
R. Kazim et al., "Intranasal Fentanyl for Postoperative Pain Management in Children Undergoing Bilateral Myringotomy and Tube Placement", Anaesth. Analg., vol. 86, S407, 1998.
F.M. Wood et al., "Patient Controlled Analgesia Using Fentanyl via the Intranasal Route for the Treatment of Procedural Pain", Journal of burn care and rehabilitation, vol. 20, p. S270, 1999.

M.J. Higgins et al., "A Physiological Model, of Fentanyl Pharmacokinetics for Various Routes of Administration", Br. J. Pharmacol. vol. 104, Suppl., p. 271P, 1991.

L. Bromley, "Recent advances in pain relief", Br. J. Hosp. Med., vol. 51, No. 8, p. 431, 1994.

U. Oral et al., "Intranasal fentanyl administration for postoperative pain relief", Br. J. Anaesth., vol. 74, Suppl. 1, p. 139, A.458, 1995.

(D25) H.W. Striebel et al., "Intranasal Fentanyl for the Therapy of Acute Breakthrough Pain in Cancer Patients, A Pilot Study", Der Schmerz, (1993) 7:174-177, © Springer-Verlag 1993, with full English translation.

(D26) "Measuring the solubility of fentanyl citrate in water", submitted by Third Party in connection with Third Party Observations Under Article 115(1) EPC received by the EPO on Nov. 1, 2007.

Akio Mizutani et al., "Effect of Nasal Midazolam with Fentanyl for Preinduction of Anesthesia and Postoperative Analgesia in Pediatric Patients", The Journal of Japan Society for Clinical Anesthesia, vol. 15, No. 5, pp. 398-401, 1995.

David F. Volles et al., "Pharmacokinetic Considerations", Critical Care Clinics, Pain Management, vol. 15, No. 1, pp. 55-75, Jan. 1999.

J.M. Alexander-Williams et al., "Novel routes for opioid administration", British Journal of Anaesthesia, vol. 81, pp. 3-7, 1998.

Margo McCaffery et al., "How to choose the best route for an opioid", Nursing, vol. 30, No. 12, pp. 34-40, 2000.

L.E. Mather et al., "Clinical Pharmacokinetics of Fentanyl and its Newer Derivatives", Clinical Pharmacokinetics, vol. 8, pp. 422-446, 1983.

Sebastiano Mercadante et al., "Alternatives to Oral Opioids for Cancer Pain", Oncology, pp. 215-217, Feb. 1999.

Sheilah A. Robertson et al., "Efficacy of the Intranasal Route for Administration of Anesthetic Agents to Adult Rabbits", Laboratory Animal Science, vol. 44, No. 2, pp. 159-165, Apr. 1994.

H. Stoeckel et al., "Pharmacokinetics of Fentanyl as a Possible Explanation for Recurrence of Respiratory Depression", Br. J. Anaesth., vol. 51, pp. 741-745, 1979.

James B. Yee et al., "Novel Drug Delivery Systems", Headache Quarterly, Current Treatment and Research, 5:2, pp. 128-134, 1994.

J.B. Streisand et al., "Newer drug delivery systems", Current Anaesthesia and Critical Care, vol. 6, pp. 113-120, 1995.

H.W. Striebel et al., "Intranasal fentanyl titration for postoperative pain management", Anesthesiology, vol. 75, No. 3A, ASA Abstracts, A671, 1991.

H.W. Striebel et al., "Intranasal fentanyl titration for pain management patient's assessment", Anesthesiology, vol. 77, No. 3A, ASA Abstracts, A853, 1992.

Charbel A. Kenaan et al., "Pharmacodynamics and Intubating Conditions of Cisatracurium in Children During Halothane and Opioid Anesthesia", Journal of Clinical Anesthesia, Original Contributions, vol. 12, pp. 173-176, 2000.

H.W. Striebel et al., "New modes of opioid administration", Der Schmerz, vol. 7, pp. 131-139, 1993.

R. Schwagmeier et al., "Midazolam pharmacokinetics following intravenous and buccal administration", Br. J. Clin. Pharmacol. vol. 46, pp. 203-206, 1998.

W.D. Mi et al., "Hypnotic endpoints vs. the bispectral index, 95% spectral edge frequency and median frequency during propofol infusion with or without fentanyl", European Journal of Anaesthesiology, vol. 16, pp. 47-52, 1999.

H.W. Striebel et al., "Self-administered intranasal meperidine for postoperative pain management", Canadian Journal of Anaesthesia, Report Information from Dialog DataStar, Thomson Dialog, vol. 42, No. 4, pp. 287-291, ISSN: 0832-610X, Apr. 1995.

H.W. Striebel et al., "A device for patient-controlled intranasal analgesia (PCINA)", Der Schmerz, vol. 9, pp. 84-88, 1995.

Rolf Schwagmeier et al., "Pharmacokinetics of Intranasal Alfentanil", Journal of Clinical Anesthesia, vol. 7, pp. 109-113, 1995.

N.I. Cherny et al., "Pharmacotherapy of cancer pain. 2. Use of opioids", Der Schmerz, vol. 9, pp. 3-19, 1995.

M. Vercauteren et al., "Intranasal sufentanil for pre-operative sedation", Anaesthesia, vol. 43, pp. 270-273, 1988.

Walter H. Striebel et al., "Intranasal Meperidine Titration for Post-operative Pain Relief", Anesth. Analg. vol. 76, pp. 1047-1051, 1993.

Third Party Observations (in English) Under Article 115(1) EPC received by the EPO on Apr. 11, 2005 in connection with the European application corresponding to the present application U.S. application.

D. Özcengiz et al., "Comparison of Intranasal Administration of Alfentanyl at Different Doses in Premedication of Children", XXXIV. Türk Anesteziyoloji ve Reanimasyon Kongresi Ku§adasi 25 Ekim-29 Ekim. PE-P9 s: 428, 2000.

H. Özbek et al., "Intranasal and Intravenous Fentanyl Administration in Postoperative Pain Treatment", Cukurova University, Faculty of Medicine, Department of Anesthesiology, Adana, XXXI. Tark Kongre Özet Kitabi; S448, Bursa, 1997.

G. Isik et al., "AG-19 Intranasal Fentanyl Administration in Postoperative Pain Treatment", Cukurova University, Department of Anesthetics, Adana, 1994.

H. Özbek et al., Postoperatif ağri tedavisinde intranazal ve intravenöz alfentanil uygulamasi, Agri Dergisi, vol. 10, No. 1, pp. 64-67, 1998.

Fentanyl 300 microgram/6 ml Inhalation, International Journal of Pharmaceutical Compounding, vol. 2, No. 2, p. 153, Mar./Apr. 1998.

Leo Latasch, M.D., Ph. D., et al., "Nasal Fentanyl Versus Nasal Sufentanil for Postoperative Analgesia in Gynecological Patients", Anesthesiology, vol. 99, A-491, 2003.

M.J. Paech et al., "A new formulation of nasal fentanyl spray for postoperative analgesia: a pilot study", Anaesthesia, vol. 58, pp. 740-744, 2003.

O. Dale et al., "Nasal administration of opioids for pain management in adults", Acta Anaesthesiologica Scandinavica, vol. 46, No. 6, pp. 759-770, 2002.

English translation of Examiner's Report dated Aug. 29, 2008 issued in connection with Japanese Patent Application No. 2002-515260 corresponding to the present U.S. application.

Advanced Doctoral Dissertation by Hans Walter Striebel entitled "Demand-adapted Intranasal Opioid Titration for Post-operative Pain Management Pharmacokinetic and Clinical Studies", presented to the Medical Faculty of the Free University of Berlin, pp. 1-171, Jun. 7, 1993, together with partial English translation thereof.

Third Party Request for Re-Examination dated Mar. 20, 2009 filed in connection with AU 2001281746 corresponding to present U.S. application.

English translation of D1: Striebel H.W. et al: Intranasales Fentanyl zur Therapie akuter Schmerzspitzen bei Karzinompatienten, Der Schmerz, 1993, 7, 174-177.

English translation of D2: Özbek, Hayri, et al: "Comparison of the Effects of Intranasal and Intravenous Fentanyl Administration on Postoperative Pain Relief" Türk Anest Rean Cem Mecmuast 25:467-470, 1997.

English translation of D3: Isik, G et al: "The effects of intranasal fentanyl and alfentanyl in postoperative pain relief" Agri Dergisi, Clit: 7, Sayi: 3, 1995.

English translation of D4: Kahvesi, Kadriye Türkay et al: "Cocuklarda Premedikasyonda intranazal midazolam, ketamin, alfentanil, fentanil, etkinliginin karsilastirilmasi" Türk Anest Rean Mecmuasi, 25: 229-304, 1997.

Laurence E. Mather et al., "Pulmonary administration of aerosolised fentanyl: pharmacokinetic analysis of systemic delivery", Br. J. Clin. Pharmacol, 46, pp. 37-43, 1998.

Martindale: The Extra Pharmacopoeia, Analgesics Anti-inflammatory Drugs and Antipyretics, published by the Pharmaceutical Press, London UK, Thirty-second edition, pp. 38-41, 1999.

(D27) Martindale the Extra Pharmacopoeia, Twenty-eighth Edition, The Pharmaceutical Press, pp. 1012-1013, 1982.

(D28) Physicians' Desk Reference, 48 Edition, pp. 1098-1100, 1994.

(D30) ABPI Compendium of Data Sheets and Summaries of Product Characteristics, With The Code of Practice for the Pharmaceutical Industry, Datapharm Publications Limited, p. 472, 1996-97.

(D34) Martindale The Extra Pharmacopoeia, Thirtieth Edition, The Pharmaceutical Press, pp. 1076-1079, 1595 and 1841, 1993.

New Pharmaceuticals, Third Edition, pp. 250-253, 1987 with English translation.

EPO Communication dated Jan. 8, 2009 with Opposition (21 pages) to grant of European patent corresponding to the present U.S. application.

Office Action dated Oct. 23, 2009 in European Application corresponding to present U.S. Application.

Re-examination report dated Oct. 29, 2009 for Australian Application corresponding to present U.S. Application.

(D 9) Peng et al., "A Review of the Use of Fentanyl Analgesia in the Management of Acute Pain in Adults", Anesthesiology, vol. 90, No. 2, pp. 576-599, Feb. 1999.

(D16a) Abstract of Finkel et al., "The effect of intranasal fentanyl on the emergence characteristics after sevoflurane anesthesia in children undergoing surgery for bilateral myrinotomy tube placement", Anesth Analg, May 2001, 92(5):1164-8.

(D21) The Oxford Turkish-English Dictionary, Third Edition, 1984, p. 122, definition for damlacik (dropper).

(D22) Extract for Fentanyl from Ph. Eur. 5.08, Jan. 2005.

(D23) Scholz et al., "Clinical Pharmacokinetics of Alfentanil, Fentanyl and Sufentanil", Clin Pharmacokinet, Oct. 31, 1996, pp. 275-292.

(D24) Extract from European Pharmacopoeia 5.0, Jan. 2005, pp. 7-8 and 1585-1586.

(D31) Letter dated Jun. 22, 2006 filed by Applicant in Australian Application corresponding to present U.S. Application.

(D32a) Abstract of Toussaint et al., "Patient-controlled intranasal analgesia: effective alternative to intravenous PCA for postoperative pain relief", Can J Anaesth, Apr. 2000, 47(4): 299-302.

(D35) Exhibit for "Solubility of Fentanyl citrate in water", dated Jul. 1, 2009 issued in Opposition in connection with European Application corresponding to present U.S. Application.

English translation of an Interrogatory dated Jun. 2, 2010 issued in connection with Japanese Patent Application No. 2002-515260 corresponding to the present U.S. Application.

Interlocutory Decision from the EPO dated Jul. 2, 2010, issued in connection with the European Patent claiming priority from the same Danish Application for which priority is claimed in the present U.S. Application.

* cited by examiner

Plasma profile i.v., i.n. single dose and i.n. titration

Elapsed time

Subject No. 1 Fentanyl profile 75 mcg

Subject No. 2 Fentanyl profile 75 mcg

Subject No. 4 Fentanyl profile 100 mcg

Subject No. 5 Fentanyl profile 100 mcg

Subject No. 6 Fentanyl profile 100 mcg

Subject No. 7 Fentanyl profile 100 mcg

Subject No. 8 Fentanyl profile 150 mcg

Subject No.9 Fentanyl profile 150 mcg

Subject No. 10 Fentanyl profile 150 mcg

Subject No. 11 Fentanyl profile 200 mcg

Subject No. 12 Fentanyl profile 200 mcg

4c Figure
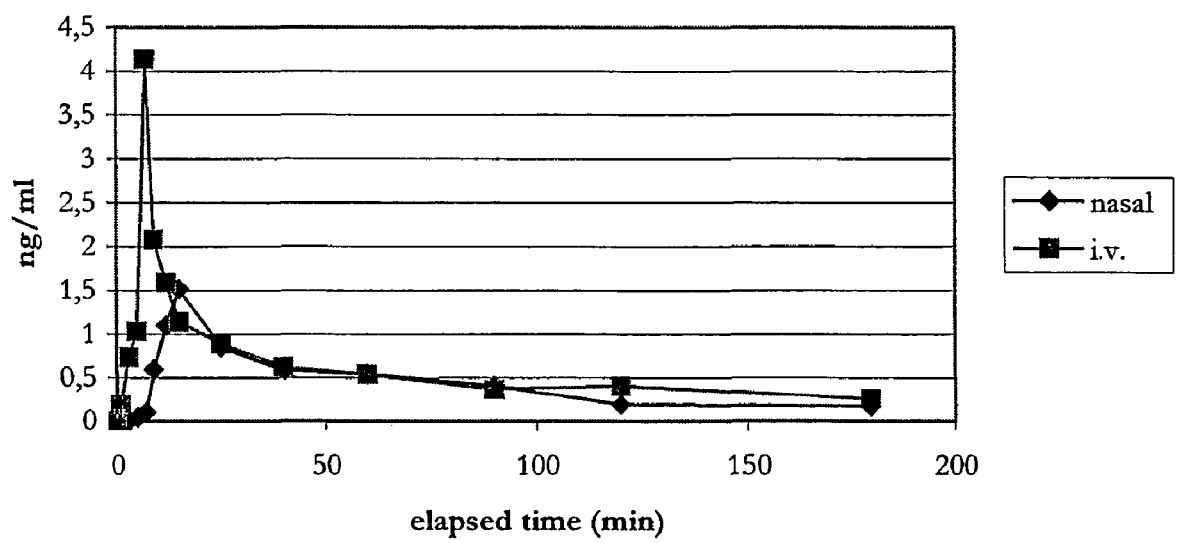
Subject No. 13 Fentanyl profile 200 mcg

PID profile, 75 mcg fentanyl

PID profile 100 mcg fentanyl

FENTANYL COMPOSITION FOR NASAL ADMINISTRATION

FIELD OF INVENTION

The present invention relates to a pharmaceutical composition for use in the treatment of acute pain such as breakthrough pain by means of a non-invasive administration of fentanyl or a pharmaceutically acceptable salt thereof, said composition being such that at least 70 µg of fentanyl is delivered in a dosage unit. The method comprises administration of a treatment dosage sufficient to treat the acute pain with time to onset of action comparable to intravenous administration. The treatment typically comprises intranasal administration of a relatively concentrated composition of fentanyl citrate. In addition, the invention relates to a pharmaceutical kit comprising a treatment dosage of fentanyl for nasal administration for treatment of acute pain together with a delivery system of an analgesic for a continuous treatment of chronic pain.

BACKGROUND OF THE INVENTION

Fentanyl is a potent narcotic analgesic with pharmacological effects similar to morphine. Fentanyl is 50 to 100 times more potent than morphine on a weight basis. Fentanyl is a mu-receptor agonist acting on receptors distributed in the brain, spinal cord and other tissues. Opioids produce both analgesia and sedation. Opiate agonists appear to prevent the release of beta-endorphin, possibly by altering the patients perceived level of pain and anxiety, although the presence of pain may still be recognised (1).

Parenteral fentanyl is indicated for anaesthesia, treating postoperative pain, and as a premedicant. Transdermal fentanyl is used for managing chronic pain in patients requiring opioids. Fentanyl lozenge/sucker (Oralet®) is indicated to induce anxiolysis and analgesia prior to surgery in pediatric and adult patients. Oral transmucosal fentanyl (Actiq®) is indicated for the management of breakthrough cancer pain in adults with malignancies who are already receiving and who are tolerant to opioid therapy for their underlying persistent cancer pain. Fentanyl Oralet® is only indicated for use in a hospital setting as an anaesthetic pre-medication in the operating room setting or to induce conscious sedation prior to a diagnostic or therapeutic procedure in other monitored anaesthesia care settings in the hospital.

In normal doses, the most common side-effects of morphine and other opioid analgesics are nausea, vomiting, constipation, drowsiness, and confusion. Tolerance generally develops with long-term use. Micturition may be difficult and there may be ureteric or biliary spasm; there is also an antidiuretic effect. Dry mouth, sweating, facial flushing, vertigo, bradycardia, palpitations, orthostatic hypotension, hypothermia, restlessness, changes of mood, hallucinations, and miosis also occur. These effects tend to occur more commonly in ambulant patients than in those at rest in bed and in those without severe pain. Raised intracranial pressure occurs in some patients. Muscle rigidity has been reported following high doses. The euphoric activity of morphine and similar compounds has led to their abuse.

Unlike morphine, fentanyl is reported not to cause significant histamine release. Transient hypotension may follow intravenous administration. Muscle rigidity in high doses may occur and may require administration of muscle relaxants; caution is advised in patients with myasthenia gravis.

It has been shown (4-7) that fentanyl administered intranasally in doses of 0.027 mg every 5 minutes, as necessary, is effective in the relief of postoperative pain and cancer pain. In this trial the drug was delivered in small dilute doses of small amounts of agent at a predetermined interval of 5 minutes.

Intranasal delivery of low concentrations and low doses of fentanyl has been performed. Concentrations and doses have been maintained low due to the risk of respiratory depression associated with high doses. Demand-adapted titration was considered to be the only method of avoiding the risk of side effects (4-7). Thus, repeated delivery of a composition of ca. 50 µg/mL of fentanyl was administered.

Animal data (rabbits) showed rapid occurring absorption by use of the nasal route. The nasal route would therefore be suitable for use in patients requiring rapid relief of severe pain. General advantages of nasal application aiming at systemic effect are ease of self-administration, supporting a health-economic argument and the self-care concept. In addition, first pass liver metabolism and gastro-intestinal metabolism is avoided.

Intravenously, doses of 50 to 150 µg/kg are indicated for anaesthesia in cardiac surgery whereas doses of 50 to 100 µg IM are effective as a pre-medication and adjunct to regional anaesthesia. Continuous intravenousinfusion of fentanyl 1.5 µg/kg/hour for 24 hours has been effective in providing postoperative analgesia without significant respiratory depression in patients who underwent hysterectomy.

Transdermal doses range from 25 to 100 µg/hr. Initial doses not exceeding 25 µg/hr are recommended (1).

Oral transmucosal fentanyl citrate is marketed as fentanyl Oralet® and Actiq® fentanyl lozenge/sucker (fentanyl Oralet®) in doses of 5 to 15 µg/kg (maximum 400 µg) is indicated to induce anxiolysis and analgesia prior to surgery for pediatric patients. Adult dosing of fentanyl Oralet® is 5 µg/kg, with a maximum dose of 400 µg. Doses of Actiq® for opioid tolerant patients with breakthrough cancer pain range from 200 to 1600 µg. The initial adult dose of Actiq® is 200 µg. From this initial dose, patients should be closely followed and the dosage not changed until the patient reaches a dose that provides adequate analgesia using a single Actiq® dosage unit per break-through cancer pain episode.

The administration of 3 mL of fentanyl citrate 500 µg/mL (318 µg/mL fentanyl base) via nebulization was effective in providing postoperative analgesia in 10 patients who underwent a variety of surgical procedures. However, duration of analgesia varied considerably from 5 to 90 minutes. This route of administration is inefficient and labour intensive and therefore is generally not recommended (1).

Fentanyl produces analgesia almost immediately following intravenous administration whereas in lozenge/sucker delivery and oral transmucosal administration, onset is seen within 15 minutes.

Fentanyl is metabolised in the liver and excreted in the urine primarily as metabolites (less than 7% unchanged drug). The half-life of fentanyl is 2 to 4 hours. Fentanyl has a distribution half-life of 10 minutes in adults and children (1).

SUMMARY OF THE INVENTION

The invention relates to a novel composition capable of delivering an effective dose of an equivalent of fentanyl through transmucosal delivery. Intravenous administration of fentanyl has numerous pragmatic disadvantages compared to transmucosal administration as well as resulting in peak plasma concentrations which are related to dangerous side effects such as depression of the respiratory system. However, intravenous administration has one major advantage over current transmucosal, oral, and pulmonary administration of fentanyl in that the time-to-onset-of-action of the intravenous administration is much faster. Current transmucosal compositions require administration of several dosage units by the pain sufferer in a "titration" method wherein the sufferer self administrates as many dosage units as required to obtain the alleviation of pain, often requiring 4-6 administrations. The consequence of this "titration" administration is a relatively long time-to-onset-of-action during which the sufferer continues to experience pain, often acute pain. The present investigators have developed a composition which administers by transmucosal delivery an effective dosage of an equivalent of fentanyl to alleviate the pain with a time-to-onset-of-action comparable to that of intravenous administration, notably after a single administration of said composition.

A first aspect of the present invention therefore relates to a pharmaceutical composition comprising fentanyl, or salts thereof, in a suitable solvent at a concentration equivalent to about 0.4 to 75 mg/mL of fentanyl.

As stated supra, the present composition is delivered as dosage unit having a concentration sufficient so as to achieve a rapid onset of action and avoiding the "titration delivery" of the agent. Thus, the dosage unit is also an important aspect of the present invention as it, in one or two delivery operations, must provide sufficient amounts of the agent. Thus, a second aspect of the invention relates to a dosage unit comprising fentanyl, or salts thereof, in a suitable solvent, having a concentration equivalent to about 0.4 to 75 mg/mL of fentanyl.

The use of a composition comprising fentanyl, or salts thereof, for the preparation of a medicament for the treatment of pain in a mammal wherein said medicament comprises a concentration equivalent to about 0.4 to 75 mg/mL of fentanyl, wherein the medicament is formulated for transmucosal administration is a further aspect of the invention.

Alternatively stated, given the amount of the agent is an important feature of the medicament, the use of a composition comprising fentanyl, or salts thereof, for the preparation of a medicament for the treatment of pain in a mammal wherein administration of said medicament comprises delivery of one or more dosage units each equivalent to about at least 70 μg of fentanyl, wherein said dosage unit is formulated for transmucosal administration is a still further important aspect of the invention. As is clear from the above, the medicament is formulated to deliver dosage units with sufficient amounts of the agent. Thus, the use of a composition comprising fentanyl, or salts thereof, for the preparation of a medicament for the treatment of pain in a mammal, wherein said medicament is formulated for transmucosal administration of a dosage unit, wherein said dosage unit comprises an amount equivalent to about at least 70 μg of fentanyl is an important aspect of the present invention.

The composition is directed to pain management. An important aspect of the invention relates to a method for treating, alleviating or lessening pain in an individual comprising the administration of a pharmaceutical composition comprising fentanyl, or salts thereof, in a dosage unit equivalent to at least 70 μg of fentanyl. Alternatively defined, this aspect of the invention relates to a method for treating, alleviating or lessening pain in an individual comprising the administration of a pharmaceutical composition comprising fentanyl, or salts thereof, wherein said composition has a concentration equivalent to about 0.4 to 75 mg/mL of fentanyl.

A still further aspect of the invention relates to a method for the administration of fentanyl or a pharmaceutically acceptable salt thereof to the circulatory system of an individual in need of acute pain relief comprising administration of a treatment dosage comprising 70 μg to 2000 μg fentanyl in a pharmaceutical vehicle for transmucosal delivery of fentanyl to a mucosal membrane of the individual.

Pain management using the composition, dosage units or methods of the invention may be paired with other technologies to form part of multi-component strategy to pain management. This strategy may, for example, utilise known technologies for the management of chronic pain and the present invention for management of pain during acute episodes of pain. Thus, a further aspect of the invention relates to a kit comprising i) composition formulated for the delivery of a dosage unit comprising 70 μg to 2000 μg of fentanyl, or pharmaceutically acceptable salts thereof for a continuous treatment of pain in a vehicle for transmucosal delivery for the treatment of acute pain; and ii) an analgesic for continuous treatment of pain.

DETAILED DESCRIPTION OF THE INVENTION

The term "fentanyl" is intended to relate to fentanyl or a pharmaceutically acceptable salt thereof. The term "equivalent to about . . . of fentanyl" is intended to relate to a specified volume, concentration, or amount of fentanyl free base provided by a volume, concentration, or amount of a salt of fentanyl. Thus the specified amount relates to the amount of fentanyl free base and not the amount of the fentanyl salt, despite the use of the salt in the composition. In a most preferred embodiment, the composition, methods and uses of the present invention comprise the use of fentanyl citrate.

The term "formulated" is intended to relate to the selection of excipients, carriers, vehicles, preservatives, stabilising agents and so forth in the preparation of medicament using said composition. The term "formulated" is furthermore intended to relate to the selection of the device for delivery of the composition or selection of containment device for administration or storing of the composition.

The term "dosage unit" relates to the composition administered in one administration by one delivery operation. In the embodiment wherein the composition is formulated for transmucosal administration by nasal delivery, a dosage unit is the volume of the composition administered or amount of agent administered by one delivery operation. A delivery operation is an operation which delivers a dosage unit. In this embodiment, a delivery operation is the administration to the nasal cavity of a dosage unit by means of a delivery system, such as a nasal spray or other means known to the person skilled in the art. Suitable devices are commercially available from e.g. Pfeiffer and Valois. The terms "dosage" and "treatment dosage" relates to the total amount of agent or volume of composition applied by means of administration of dosage units during a treatment. A treatment relates to the administration of the composition during a single episode of pain, said episode lasting until alleviation of pain.

The term "time-to-onset-of-action" is intended to mean the moment wherein the patient begins to experience pain relief, usually as a result of sufficient plasma concentrations of fentanyl. Sufficient plasma concentrations to achieve analgesia varies amongst patients, amongst patient classes and types and nature of pain experienced. The "action" in "time-to-onset-of-action" is pain relief.

The term "duration-of-action" relates to the time throughout which pain relief is experienced by the patient.

The pharmaceutical composition of the invention comprises fentanyl, or salts thereof, in a suitable solvent at a concentration equivalent to about 0.4 to 75 mg/mL of fentanyl. The composition is suitably formulated for transmucosal administration, typically to deliver fentanyl through the nasal mucosa.

The composition of the invention typically has a concentration equivalent to about 0.5 to 20 mg/mL of fentanyl, preferably 0.6 to 15 mg/mL, 0.7 to 12 mg/mL, more preferably 0.75 to 10 mg/mL of fentanyl, most preferably 0.75 to 8 mg/mL. Suitable compositions have a concentration equivalent to about at least 0.5 mg/mL of fentanyl, such as 0.7 mg/mL, such as 0.75 mg/mL, such as about 1 mg/mL, about 1.5, about 2, about 2.5, about 3, about 3.5, about 4, about 4.5, about 5, about 5.5, about 6, about 6.5, about 7, about 7.5, and about 8 mg/mL.

As stated, the composition is delivered as a dosage unit wherein administration comprises delivery of one or more dosage units of about 10 to 500 µL, such as 10 to 200 µL, preferably about 50 to 150 µL. In the embodiment wherein delivery is via the nasal mucosa, a delivery unit corresponds to the volume provided by a squirt or spray, depending on the device utilised for delivery of the composition and dosage unit.

In the event wherein the nasal application exceeds about 200 µl, there may be a risk of loss of the formulation to the larynx or loss through the nostrils. Accordingly, the formulation for nasal administration should preferably not exceed 200 µl. Accordingly, a preferred volume according to the invention includes a volume selected from 10 µl, 25 µl, 50 µl, 75 µl, 100 µl, 150 µl, 200 µl, 250 µl, 300 µl, and 350 µl, and 400 µl where the volume may be delivered to both nostrils if preferred.

In a preferable embodiment, said composition is formulated for nasal delivery of a dosage unit comprising an equivalent to at least about 70 µg of fentanyl, such as 80, 90, or 100 µg, such as 125, 150, 200, 250, or 300 µg, such as 350, 400, 450, 500 µg, such as 550, 600, 650, 700, 750, 800, 850, 900, or 950 µg, such as 1000, 1050, 1100, 1250, or 1300 µg, such as 1350, 1400, 1450, 1500 µg, such as 1550, 1600, 1650, 1700, 1750, 1800, 1850, 1900, or 1950 µg, such as a dosage unit equivalent to 2000 µg of fentanyl.

Alternatively defined, the composition is formulated for transmucosal delivery of a dosage unit equivalent to about 70 to 2000 µg of fentanyl, such as 70 to 1800 µg, preferably 70 to 1500 µg, such as 70 to 1200 µg, particularly preferably 70 to 1000 µg, more preferably 70 to 500 µg, most preferably equivalent to 75 to 300 µg of fentanyl.

The present invention further relates to a method for the administration of fentanyl or a pharmaceutically acceptable salt thereof to the circulatory system of an individual in need of acute pain relief. The treatment dosage is such that to be sufficient to treat the acute pain within a narrow time-to-onset-of-action. In order to result in a plasma concentration sufficient to treat acute pain, a treatment dosage will normally be within a range of at least 70 µg and up to 2000 µg fentanyl. In order to have the fentanyl administered to the circulatory system within an acceptable period and without delivering the fentanyl by injection, the fentanyl is administered to a mucosal membrane of the patient in a pharmaceutical vehicle for transmucosal delivery of the fentanyl.

The sufficient pain relieving dosage may vary between the patients as well as in the individual patient. For treatment of relative moderate acute pain, the treatment dosage may comprise at least 70 µg fentanyl, preferably at least 100 µg fentanyl, more preferred at least 150 µg fentanyl, such as 200 µg fentanyl. For treatment of more severe acute pain, the treatment dosage comprises at least 250 µg fentanyl, preferably at least 300 µg fentanyl, more preferred at least 400 µg fentanyl, such as 500 µg fentanyl. In cases where the patient suffers from heavy acute pain or the patient has developed tolerance to fentanyl higher dosages may be required and administered according to the present invention. Such high dosages include treatment dosage comprising 600 µg fentanyl, preferably at least 800 µg fentanyl, more preferred at least 1000 µg fentanyl, such as at least 1200 µg fentanyl. Even higher dosages may be desired such as treatment dosages of 1300 µg fentanyl, preferably at least 1400 µg fentanyl, more preferred at least 1500 µg fentanyl, such as 1600 µg fentanyl. The high dosage treatment may involve patients which are receive regular treatment with opioid analgesics, and it is believed that a few numbers of patients may need treatment dosage comprising from 1800 to 2000 µg fentanyl.

As stated, the compositions of the invention for transmucosal delivery are of a more potent concentration than compositions known to the person skilled in the art. Thus, treatment dosages effective for alleviating pain are typically achieved by administration comprising delivery of not more than two dosage units. In a preferred embodiment, the composition is formulated such that not more than two dosage units comprise a treatment dosage. The composition, although being more potent, significantly reduces the risk of adverse effects such as depression of the respiratory system, as shown in the Examples.

The composition is intended for the treatment, alleviation or lessening of acute or breakthrough pain, such as benign acute pain episodes like angina pectoris, colic/biliary pain, trauma, postoperative pain, dental pain, orofacial pain, sympathetic pain syndrome, pancreatic pain, myocardial infarction pain, back pain, cancer pain, pain during or after change of dressing and pre-operative anesthesia.

It is an important aspect of the invention that the pain relief is always obtained very shortly upon administration of fentanyl. Accordingly, the relief of the acute pain should be obtained very shortly after administration of the first delivery of the dosage unit or treatment dosage such that the administration of composition has a time-to-onset-of-action of less than 10 minutes, such as less than 9 minutes, preferably less than 8 minutes.

A very important advantage of the present invention is, in addition to the very short a time-to-onset-of-action, that the pain relief is maintained for at least 30 minutes. Thus, administration of the composition has a duration-of-action maintained throughout a period of at least 30 minutes. Although, in some instances, it is preferable for the duration-of-action to be maintained throughout a period of at least 1 hour or at least 1.5 hours upon administration of the treatment dosage, given acute pain typically only lasts for brief periods, it is often preferable for the duration of action to be maintained for at least 30 minutes but throughout a period of not greater than 90 minutes, preferably maintained throughout a period of at least 30 minutes and throughout a period of not greater than 60 minutes.

This is a further advantage of the present invention. The composition is able to have a rapid onset-of-action whilst providing a sufficiently long duration-of-action but without an unnecessarily protracted period of effect.

The composition has a pseudo "sustained release" effect in comparison to intravenous administration which has a very rapid onset of action but with a very short duration of action. The intravenous administration results in a higher peak plasma concentration of fentanyl. The intravenously administered fentanyl results in a peak plasma concentration directly proportional to the amount of fentanyl administered, i.e a high $C_{max}$. Conversely, the "titration" administration of a composition intranasally as described by Striebel (references 4-7) has a slower onset of action and unnecessarily long duration of action.

The composition, upon administration, typically has a bioavailability of no less than 75% that of intravenous administration, preferably no less than 80% of intravenous administration, more preferably no less than 90% of intravenous administration. Bioavailability may be determined by its AUC, as is known to the person skilled in the art.

The method of the invention comprises the administration of dosage units comprising from about 70 to 2000 kg of fentanyl, said administration preferably resulting in a $C_{max,\,nasal}/C_{max,\,iv}$ ratio which decreases with increasing dosage units delivered of equal amounts of fentanyl, within the treatment dosage range of from about 70 to 2000 µg.

In a further aspect, the composition, dosage unit, use and method of the invention is characterised by the effect of the treatment on the acute pain as measured as described herein. One way to record pain according to the invention comprises the measurement of onset of pain relief. Just before administration of the treatment the time is measured e.g. by starting a stopwatch. When the subject is certain of feeling a meaningful pain relief the time is recorded e.g. by stopping the stopwatch. The composition of the invention, upon administration, has a pain reduction score in the range of 2 to 7, such as 2, 3, 4, 5, 6, and 7, preferably such as 3, 4, 5, and 6, as measured by PID upon delivery of no more than two dosage units, preferably after delivery of one dosage unit.

At least 50% of subjects obtaining onset within 15 minutes after administration of treatment will be considered a success. Likewise the duration of effect may be measured as the difference between onset of effect and the time point where the subject declares the effect to cease or the time when the subject takes rescue medication, whatever comes first. Duration of pain relief of at least half an hour experienced by at least 50% of the subjects will be considered a success.

Another measurement is the Pain Intensity (PI) scored on an 11-point numeric rating scale (0=no pain, 10=unendurable pain). $PI_i$ is the pain intensity at the time point $T_i$. The $PI_i$ is measured at one or more of the following time points ($T_i$) before treatment (baseline), at the time of meaningful pain relief, every 15 minutes after administration of treatment for the two first hours, and every 30 minutes for the next two hours. A 40% decrease of mean PI within 15 minutes after treatment will be considered a success. Naturally other time points may and intervals may be selected.

$PI_0$ is the baseline pain intensity (scored on a scale as disclosed above) before administration of treatment (at time $T_0$). Pain Intensity Difference (PID) is the $PI_0$ compared to the pain intensity at time points after the administration of treatment ($PI_i$). A mean PID of 2 obtained within 15 minutes after administration will be considered a success.

A further measurement is the area under the PID curve or the Sum of Pain Intensity Difference (SPID), PI being measured at the time points disclosed above. A mean 4-hour SPID of 3 will be considered a success.

One method relates to a pain intensity scale as disclosed herein wherein pain relief is measured as a pain intensity difference (PID) of at least 30%, such as at least 40% based on a pain score measured close to the time of the administration $PI_0$ and a pain score measured at the time $PI_i$ after administration. The time after administration may be selected from the time of one or more of the following times 3 minutes, 5 minutes, 7 minutes, 10 minutes, 15 minutes, 20 minutes, and 30 minutes upon administration. These times is used when the purpose of the measuring is to evaluate the immediate effect of the administration. If a measurement of the duration of treatment is desired, the pain relief is measured as a pain intensity difference (PID) based on a score measured immediately before the administration $PI_0$ and at the time $PI_i$ after administration, the time after administration being selected from the time 45 minutes, 60 minutes, 75 minutes, 90 minutes, and 120 minutes upon administration. One alternative is to measure an effect from a given time after administration to a later time, and in this respect the desired time range is selected individually.

The pain relief score may be measured in accordance with the method disclosed herein or on a scale of 1-100% wherein 100% is a pain described by the patient as unbearable and 0% is no pain at all. It is preferred that the score is at least 30% from the start to the maximum analgesic effect is obtained.

A further measurement is as explained above the sum of pain intensity difference (SPID) based on a score measured immediately before the administration $PI_0$ and at the time $PI_i$ after administration, the time after administration being selected from the time any time as desired and includes the times as disclosed herein. In a preferred embodiment, the sum of pain intensity difference is measured from at least 2 values measured during a period of at least 30 minutes, preferably at least during 45 minutes, preferable at least during 60 minutes such as during 90 minutes. Furthermore, the sum of pain intensity difference may be measured from at least 5 values such as at least from 7 values, preferable from at least 10 values such as from 11, 12 or 13 values.

The peak plasma concentrations achieved by intravenous administration of fentanyl are associated with side effects such as depression of the respiratory system. As shown in FIGS. 6a-6d, the peak plasma concentrations of the present invention are sufficient to provide the desired effect (as well as being achieved rapidly and sustained sufficiently long). Thus, the invention further relates to a composition wherein said administration of the no more than two dosage units has a peak plasma concentration of no less than 5% and no more than 75% of the peak plasma concentration obtained by intravenous administration of said dosage unit(s), within the treatment dosage range of from about 70 to 2000 µg, preferably a peak plasma concentration of no less than 30% and no more than 75% of the peak plasma concentration obtained by intravenous administration of said dosage unit(s), within the treatment dosage range of from about 70 to 2000 µg.

In an interesting aspect of the invention, repeated administration of dosage units does not result in increases in peak plasma levels. In intravenous administration, repeated administration continue to elevate the plasma concentrations to undesired high levels. Conversely and advantageously, again possibly due to pseudo sustained release characteristics of the mode of administration, repeated transmucosal administration of a dosage unit does not continue to elevate the plasma concentration. Thus, in an interesting embodiment of the invention, the method is such that administration of the medicament results in a $C_{max,\,nasal}/C_{max,\,iv}$ ratio which decreases with increasing dosage units when comparing equal amounts of fentanyl delivered by both modes of administration (nasal vs. intravenous), within the treatment dosage range of from about 70 to 2000 µg.

The absorption of fentanyl from mucosal membranes is overall very fast resulting in good availability of the drug. However, according to the present invention the nasal mucosal membrane is preferred. In addition to the convenience of this administration route for the patient, the olfactory area of the nose is in close proximity to the brain. Nevertheless, the treatment dosage may also be administered to a mucosal membrane selected from one or more of the buccal mucosal membranes, the mucosal membrane of the respiratory tract, such as the tracheal mucosa and/or the pulmonary mucosal membrane. In a further aspect of the invention the treatment dosage may be administered to more than one location in the same treatment or the patient may choose the administration route on an individual basis. Acute pain during night may be treated with buccal administration if the nasal administration implies an irritation of the nose.

The composition preferably comprises fentanyl as its fentanyl citrate salts.

fentanyl citrate is easily soluble in water, accordingly a suitable vehicle for transmucosal delivery includes a vehicle comprising water, such as a vehicle which comprises as much as about 95%-100% water.

The composition typically comprises a solvent selected from the group comprising isotonic saline, water, polyethylene glycol, or combinations thereof.

However, use of a vehicle comprising a suitable polymer, preferably a pharmaceutical vehicle comprising n-ethylene glycol (PEG) may be preferred due to a better sprayability of a liquid comprising a polymer. The PEG is preferably one with relative low molecular weight including ethylene glycol represented by the formula $H(OCH_2CH_2)_pOH$, wherein p is an integer in the range of 1 to 14. Such PEG includes PEG 200, PEG 300 and PEG 400. Especially PEG 200 and 300 are preferred.

Other preferred polymers for the pharmaceutical vehicle for transmucosal delivery of the fentanyl includes one or more substances selected from n-glycofurols represented by the formula I

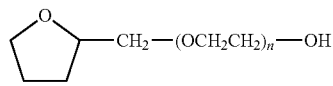

preferably wherein n is an integer in the range of 1 to 8, and more preferred 1 or 2; or mixtures thereof. The amount of n-ethylene glycol and/or n-glycofurol contained in the vehicle may be between 0.5 to 100 w/w %. The beneficial effects of the polymer include increased stability of the fentanyl. However, it is preferred that the amount of n-ethylene glycol and/or n-glycofurol contained in the vehicle is at the most 30% w/w, such as at the most 25% w/w, preferable at the most 15% w/w such at the most 10% w/w, such as the most 5% w/w. The lowest concentration of the polymer is preferred in formulations with a high concentration of fentanyl is desired.

The pharmaceutical vehicle according to the invention also includes the ones wherein the amount of n-ethylene glycol and/or n-glycofurol contained in the vehicle is at the most about 100% w/w, preferable at the most 80% w/w, such as the most 50% w/w. The highest concentration of the polymer is preferred in formulations with a low concentration of fentanyl is desired.

The increased stability to the fentanyl in the vehicle obtained by the presence of ethylene glycol and/or n-glycofurol relates to a reduced effect on radiation to the fentanyl in the vehicle. The presence of the polymer is believed to increase the resistance for light stress and possibly also to temperature stress by 1-2.5% per week or about 2-10% within one month.

A further and very important issue according to the invention is the effect obtained with respect to a decreased adsorption of the fentanyl to the surfaces of the devices used for delivery and/or the utensils used for production. When comparing a vehicle comprising the n-ethylene glycol and/or n-glycofurol not comprising the polymeric compound and/or compared with a corresponding vehicle where the n-ethylene glycol and/or n-glycofurol is replaced with water, the n-ethylene glycol and/or n-glycofurol comprising vehicle provide a higher degree of active substance. The difference in loss may be within 1-20% depending on the specific device.

A dosage unit of the invention comprises fentanyl, or salts thereof, in a suitable solvent, at a concentration equivalent to about 0.4 to 75 mg/mL of fentanyl. Alternatively defined, a dosage unit is about 10 to 500 µL, such as about 10 to 200 µL, preferably about 50 to 150 µL of the composition of the invention. A dosage unit is administered to the patient and the amounts of fentanyl administered to the individual is an important feature of the invention.

A dosage unit is preferably formulated for transmucosal administration, preferably wherein transmucosal administration comprises delivery of fentanyl through the nasal mucosa.

As stated, a dosage unit comprises sufficient agent such that, whereupon administration of the composition provides a pain reduction score in the range of 2 to 7, such as 2, 3, 4, 5, 6, and 7, preferably such as 3, 4, 5, and 6, as measured by PID upon delivery of no more than two dosage units, preferably after delivery of one dosage unit.

The method of the invention relates to the treatment, alleviation or lessening of acute or breakthrough pain, such as benign acute pain episodes like angina pectoris, colic/biliary pain, trauma, postoperative pain, dental pain, orofacial pain, sympathetic pain syndrome, pancreatic pain, myocardial infarction pain, back pain, cancer pain, pain during or after change of dressing and pre-operative anesthesia.

Alternatively defined, the method comprises the administration of fentanyl or a pharmaceutically acceptable salt thereof to the circulatory system of an individual in need of acute pain relief wherein said administration comprises administration of a treatment dosage of no more than 2 dosage units each comprising 70 µg to 2000 µg of fentanyl in a pharmaceutical vehicle for transmucosal delivery of fentanyl to a mucosal membrane of the individual.

As was implied supra, important aspects of the invention relate to the use of a composition comprising fentanyl, or salts thereof, for the preparation of a medicament for the treatment of pain in a mammal wherein administration of said medicament comprises delivery of one or more dosage units each equivalent to about at least 70 µg of fentanyl, wherein said dosage unit is formulated for transmucosal administration and to a method for treating, alleviating or lessening pain in an individual comprising the administration of a pharmaceutical composition comprising fentanyl, or salts thereof, in a dosage unit equivalent to at least 70 µg of fentanyl.

Alternatively defined, the invention relates to the use of a composition comprising fentanyl, or salts thereof, for the preparation of a medicament for the treatment of pain in a mammal, wherein said medicament is formulated for transmucosal administration of a dosage unit, wherein said dosage unit comprises an amount equivalent to about at least 70 µg of fentanyl.

Similarly, the use of a composition comprising fentanyl, or salts thereof, for the preparation of a medicament for the treatment of pain in a mammal wherein said medicament comprises a concentration equivalent to about 0.4 to 75 mg/mL of fentanyl, wherein the medicament is formulated for transmucosal administration and a method for treating, alleviating or lessening pain in an individual comprising the administration of a pharmaceutical composition comprising fentanyl, or salts thereof, wherein said composition has a concentration equivalent to about 0.4 to 75 mg/mL of fentanyl are further important aspects of the invention.

High peak plasma concentrations are associated to the serious side effects related to opioid analgesia. It is thus an object of the invention to provide a composition and, wherein said administration of the no more than two dosage units has a peak plasma concentration of no less than 5% and no more than 75% of the peak plasma concentration obtained by intravenous administration of said dosage unit(s), within the treatment dosage range of from about 70 to 2000 μg, preferably a peak plasma concentration of no less than 30% and no more than 75% of the peak plasma concentration obtained by intravenous administration of said dosage unit(s), within the treatment dosage range of from about 70 to 2000 μg.

An important feature of the present invention is that analgesic levels are reached not by a titration of the composition but by administration of only one or at most two dosage units. Thus, in a preferred embodiment, administration of no more than two dosage units provides a peak plasma concentration of no less than 5% and no more than 75% of the peak plasma concentration obtained by intravenous administration of said dosage unit(s), at treatment dosages in the range of from about 70 to 2000 μg. In a more preferred embodiment, administration of no more than two dosage units provides a peak plasma concentration of no less than 30% and no more than 75% of the peak plasma concentration obtained by intravenous administration of said dosage unit(s), within the treatment dosage range of from about 70 to 2000 μg.

Another aspect of the invention relates to the importance of reducing the peak plasma concentration of fentanyl without diminishing the intended analgesic effect. As it has been stated, an important feature of the present invention is providing a full analgesic dosage sufficient for alleviating pain by means of one or at most two delivery operations comprising administering at most two dosage units, rather than the "titration" of stepwise administration of repeated smaller dosages. The present method provides higher plasma concentrations and faster analgesia. However, in the case of extreme pain, it is anticipated that a treatment dosage may require more than two delivery operations of the dosage units of the present invention; the dosage units comprising at least 70 μg of fentanyl. These repeated administrations do not require the patient to await any protracted period of time or an effect to take place before a repeated self-administration. The division of the treatment dosage is primarily for the purpose of decreasing the value of the peak concentration without decreasing the treatment dosage. Alternatively, the dosage units may then be customised to meet the needs of the patient so as to comprise higher doses of fentanyl. In either embodiment, high peak plasma concentrations are intrinsically avoided by the pseudo slow and sustained release characteristics of transmucosal delivery, as shown in FIGS. 1, and 1A-4C.

Accordingly, in a suitable embodiment delivery of the treatment dosage may be divided into administration of no more than 4 dosage units administered within no more than 15 minutes, each administration comprising at least 70 μg of fentanyl, preferably no more than 3, typically no more than 2, such as 2 or 1. In the embodiment wherein administration of the treatment dosage comprises administration of more than 2 dosage units, the last administered dosage may be administered on a time when the effect of the first individual dosage is decreased to such a level that the maximum analgesic effect obtainable with the treatment dosage is lowered substantially. For a maximum analgesic effect with a given treatment dosage of fentanyl, the divided treatment dosage is administered within at the most 5 minutes, preferably within 3 minutes or 2 minutes. Irrespective of the number of minutes during which administration of the treatment dosage of the invention is performed, the important features of a decrease in the maximum peak plasma concentration and fast onset-of-action are obtained.

Accordingly, in one embodiment, the method according to present invention relates to a treatment regimen wherein the divided treatment dosage upon administration of the individual dosage unit quantities of the treatment dosage results in a peak plasma concentration which is substantially lower than the peak plasma concentration of the treatment dosage administered as a single dosage.

In an interesting aspect of the invention, repeated administration of dosage units does not result in increases in peak plasma levels. In intravenous administration, repeated administration continue to elevate the plasma concentrations to undesired high levels. Conversely and advantageously, again possibly due to pseudo sustained release characteristics of the mode of administration, repeated transmucosal administration of a dosage unit does not continue to elevate the plasma concentration. Thus, in an interesting embodiment of the invention, the method is such that administration of the medicament results in a $C_{max,\ nasal}/C_{max,\ iv}$ ratio which decreases with increasing dosage units when comparing equal amounts of fentanyl delivered by both modes of administration (nasal vs. intravenous), within the treatment dosage range of from about 70 to 2000 μg.

With respect to nasal administration it is very convenient to divide the treatment dosage into one or more dosages for each nostril. Accordingly, one aspect of the invention relates to a treatment dosage which is divided into at the most 3 to 4 individually dosage unit quantities, preferably into 2 or 1 individually dosage unit quantities.

A suitable administration form of the composition comprising the fentanyl is fentanyl dissolved, dispersed or suspended in a dosage unit quantity volume of 50-400 μl whereby the fentanyl may be administered to the mucosal membrane of the nose in a dosage unit quantity volume of 25-200 μl per nostril. Examples of suitable compositions is disclosed in the examples and includes a vehicle wherein the treatment dosage of fentanyl is comprised in a solution of 10 mg/ml in a vehicle comprising 5% PEG.

The preferred method for transmucosal delivery according to the present invention is the nasal route whereby a bioavailability of at least 50% may be obtained, such as at least 60% and preferably about 70%. Thus, a composition preferably has a bioavailability of no less than 75% that of intravenous administration, preferably no less than 80% of intravenous administration, more preferably no less than 90% of intravenous administration.

As stated, the method of the invention relates to the administration of fentanyl so as to achieve high plasma concentrations. However, peak plasma concentrations at levels of those achieved by intravenous administration are preferably avoided. Thus, in a preferred embodiment, the method is such that administration of the no more than two dosage units has a peak plasma concentration of no less than 5% and no more than 75% of the peak plasma concentration obtained by intravenous administration of said dosage unit(s), within the treatment dosage range of from about 70 to 2000 μg, preferably a peak plasma concentration of no less than 30% and no more than 75% of the peak plasma concentration obtained by intravenous administration of said dosage unit(s), within the treatment dosage range of from about 70 to 2000 μg.

The treatment regimen according to the invention is relevant for patients suffering from acute pain such as post-operative pain, pain after accidents and break through pain.

The treatment regimen according to the invention is especially relevant for patients suffering from break through pain despite a suitable continuing analgesic treatment, inter alia where the patient further receives an analgesic administered in a substantially regular regimen. Such regular regimen may be of any conventional manner and may include fentanyl or other analgesics. In one embodiment, the analgesic in the substantially regular regimen is an opioid or opioid analogue or a pharmaceutically acceptable salt thereof including fentanyl. The analgesic, such as fentanyl, of the substantially regular regimen may be administered orally, by the transdermal route or by depot devices, or by other conventional means well known in the art.

In one very interesting aspect of the invention, the substantially regular regimen includes fentanyl or a pharmaceutically acceptable salt thereof administered in a transdermal patch.

One important aspect of the invention is to provide the patient with a tool for optimising the treatment of acute pain irrespectively of an underlying analgesic treatment. By administration of the full treatment dosage it is possible to provide the individual patient with a relative plasma concentration of fentanyl corresponding to the pain intensity of the individual patient. When the patient recognises the break-through pain or plans activities developing pain with a certain degree the relevant treatment dosage may be administered in advance or at least before the pain is severe and on a case to case basis. Other patients may know the treatment dosage which is sufficient and divide the dosage as explained above if relevant for avoiding side effects due to a too high peak plasma concentration of the administered treatment as a single dosage.

Accordingly, in one aspect the present invention relates to a method for treating acute pain wherein the patient measures pain intensity regularly by use of a score and upon a pain score exceeding a predetermined value administers a treatment dosage of fentanyl relevant for the individual patient and the pain intensity. In other words the treatment dosage may be individually correlated to the relative pain intensity as measured by the patient himself.

The use of fentanyl according to the invention includes formulations wherein the treatment dosage of fentanyl is delivered to the mucosal membrane in the form of a solution, dispersion, emulsion, suspension, bioadhesive and non-bioadhesive gel, powder, micropheres, bioadhesive and non-bioadhesive patches or in other forms suitable for transmucosal delivery well known in the art including lozenges and lollipops.

The fentanyl is primarily administered by use of a device suitable for delivery of liquid, semi-solid or powder formulations to the mucosal membrane in question and includes use of drops, sprays, aerosols, insufflators, inhalators and patches.

The present invention further relates to a pharmaceutical composition comprising a treatment dosage of dosage comprising 70 μg to 2000 μg fentanyl or a pharmaceutically acceptable salt thereof in a pharmaceutically acceptable vehicle having a total volume of 1-2000 μl or a total weight of 1-2000 μg for use in treatment of acute pain. The preferred fentanyl is fentanyl citrate in vehicle selected from water, n-ethylene glycol (PEG) and from n-glycofurol and mixtures thereof. The preferred ethylene glycol is represented by the formula $H(OCH_2CH_2)_pOH$ wherein p is an integer in the range of 1 to 14 and includes PEG selected from PEG 200 and PEG 300 and 400. PEG 300 and 200 being most preferred. The n-glycofurols being represented by the formula I shown herein, wherein n is an integer in the range of 1 to 8, preferable in which n is mainly 1 and 2.

The pharmaceutical composition according to present invention includes a composition wherein the amount of n-ethylene glycol and/or n-glycofurol contained in the vehicle is between 0.1 to 100 w/w.

Vehicles and excipients suitable for transmucosal delivery include salts of bile acids such as glycocholate, taurocholate and deoxycholate; cyclodextrins; chitosan; polysaccharides; lectins such as lycopersicon esculentum agglutinin, wheat germ agglutinin and urtica dioica agglutinin; bacterial invasins; fusidic acid derivatives; sodium taurodihydrofusidate (STDHF); phospholipids; lysophosphatidylcholine (LPC); didecanoyl-L-phosphatidylcholine (DDPC); vegetable oils such as coconut oil, groundnut oil and almond oil; benzyl alcohol; bacitracin; sodium hyaluronate; hyaluronic acid; polyacrylic acid and derivatives thereof; methylcellulose; microcrystalline cellulose (MCC); carboxymethyl cellulose; ethyl(hydroxyethyl)cellulose (EHEC); hydroxypropylmethylcellulose (HPMC); plastoid L50; poloaxmers; propylene glycols; and fatty acids.

Pain management using the composition, dosage units or methods of the invention may be paired with other technologies to form part of multi-component strategy to pain management. This strategy may, for example, utilise known technologies for the management of chronic pain and the present invention for management of pain during acute episodes of pain. Thus, a further aspect of the invention relates to a kit comprising
i) composition formulated for the delivery of a dosage unit comprising 70 μg to 2000 μg of fentanyl, or pharmaceutically acceptable salts thereof for a continuous treatment of pain in a vehicle for transmucosal delivery for the treatment of acute pain; and
ii) an analgesic for continuous treatment of pain.

In a preferred kit, the analgesic for continuous treatment of pain is fentanyl or a pharmaceutically acceptable salt thereof in a form suitable for transdermal delivery such as a patch.

A further aspect of the invention relates to use of a treatment dosage of fentanyl or a pharmaceutically acceptable salt thereof comprising 70 μg to 2000 μg fentanyl in a pharmaceutical vehicle for transmucosal delivery, for the preparation of a medicament for treating acute pain in a patient in need thereof by administering said treatment dosage to a mucosal membrane of the patient.

For the purposes of pain management, the individual may be further administered an analgesic. The analgesic may be any known to the person skilled in the art such as those selected from the group comprising gold compounds such as sodium aurothiomalate; non-steroidal anti-inflammatory drugs (NSAIDs) such as naproxen, diclofenac, flurbiprofen, ketoprofen, and ketorolac; opioid analgesics such as codeine, dextropropoxyphene, dihydrocodeine, morphine, diamorphine, hydromorphone, methadone, pethidine, oxycodone, levorphanol, fentanyl and alfentanil, para-aminophenol derivatives such as paracetamol; and salicylates such as aspirin. In a preferred embodiment, wherein the analgesic is fentanyl, or salts thereof.

From the Examples, it can be seen that the fentanyl composition of the invention, formulated for nasal administration, has very similar analgesic properties to formulations for intravenous administration in terms of relation to pain intensity, pain intensity difference and sum of pain intensity difference. Results indicated that total analgesia obtained with the two formulations did not differ. These observations and the benefits of the nasal route of administration make nasal fentanyl a most promising new way of treating pain either used alone or as supplementary pain therapy.

With regards to time-to-onset-of-action, in obtaining analgesia to acute pain, a quick onset of effect is important. From the Examples and FIG. 5, it can be seen that the median time to onset in the present trial was 1 min after intravenous administration and 7 min after nasal administration. In real life situations it takes time before an intravenous injection can be prepared and given by a nurse or doctor whereas nasal administration can be handled by the patients themselves immediately after the need of analgesia is recognised. Thus the fastest pain relief may well be obtained after nasal self administration of fentanyl.

With regards to duration-of-action, duration of analgesic effect was found to be 49 min after intravenous administration and 56 min after nasal administration of the composition of the invention. Duration of analgesia after a single intravenous dose (up to 100 μg) has been found to be 30-60 min (16). After i.m. administration duration may be 1-2 hours (16). A recent publication elucidated break-through pain (BTP) in hospice patients in which 72% of the BTP episodes lasted less than 30 min (16).

Although the use of plasma concentrations of fentanyl may be clinically useful, plasma levels do not reflect patient sensitivity to fentanyl and therefore should not be used as a sole determinant of efficacy or toxicity. $C_{max-nasal}$ in the exploratory population increased from 0.7 ng/ml for 75 μg to 1.7 ng/ml for 200 μg fentanyl. In opioid-naive patients, analgesia has been known to be experienced in the range of fentanyl plasma concentrations of 0.2 to 1.2 ng/mL (16), confirming that this study reached therapeutic analgesic plasma concentrations of fentanyl. The smaller $C_{max-nasal}$ may result in a more favourable side effect profile for nasally administered fentanyl in regard to side effects related to plasma concentration.

Notably, mean $T_{max}$ (the time it takes to reach maximum plasma concentrations) in the exploratory population using the composition of the present invention, was 12.8 min for nasal and 6.0 min for intravenous administration. However, as can be seen from the illustrative examples of Table 1, even at 75 μg, analgesic levels of 0.2 to 1.2 ng/mL (if one basis oneself on (16)) were achieved within 3 minutes. A stated however, the median time to onset was 7 min after nasal administration

BRIEF DESCRIPTION OF TABLES AND FIGURES

Table 1 compares the plasma concentrations of illustrative patients undergoing treatment with 75 μg of fentanyl by means of nasal administration to those receiving 75 μg of fentanyl by means of intravenous administration. Data points are plotted in FIGS. 1A, 1B, and 1C.

Table 2 compares the plasma concentrations of illustrative patients undergoing treatment with 100 μg of fentanyl by means of nasal administration to those receiving 100 μg of fentanyl by means of intravenous administration. Data points are plotted in FIGS. 2A, 2B, 2C and 2D.

Table 3 compares the plasma concentrations of illustrative patients undergoing treatment with 150 μg of fentanyl by means of nasal administration to those receiving 150 μg of fentanyl by means of intravenous administration. Data points are plotted in FIGS. 3A, 3B and 3C.

Table 4 compares the plasma concentrations of illustrative patients undergoing treatment with 200 μg of fentanyl by means of nasal administration to those receiving 200 μg of fentanyl by means of intravenous administration. Data points are plotted in FIGS. 4A, 4B and 4C.

Table 5 compares pain intensity (PI) scores and pain intensity difference (PID) scores of intranasal administration to intravenous administration at 75 μg of fentanyl of individual patients. PID values are plotted in FIG. 6a.

Table 6 compares pain intensity (PI) scores and pain intensity difference (PID) scores of intranasal administration to intravenous administration at 100 μg of fentanyl of individual patients. PID values are plotted in FIG. 6b.

Table 7 compares pain intensity (PI) scores and pain intensity difference (PID) scores of intranasal administration to intravenous administration at 150 μg of fentanyl of individual patients. PID values are plotted in FIG. 6c.

Table 8 compares pain intensity (PI) scores and pain intensity difference (PID) scores of intranasal administration to intravenous administration at 200 μg of fentanyl of individual patients. PID values are plotted in FIG. 6d.

FIG. 1 illustrates the differences in plasma profiles over time of the three compared methods and compositions. Intravenous administration results in a sharp peak providing a rapid onset of action. However, the plasma levels quickly decrease as well. The high peak concentrations of intravenous administration are associated with the adverse side effects of the treatment. Conversely, the "titration" treatment described in (4-6), provides peak concentrations after a period of time considered to be too long by some pain sufferers. The time to onset of action is much longer than intravenous administration or the method of the invention. The composition and method of the present invention provides relatively fast onset of action and peak plasma concentrations, as well as having an extended duration of effect as shown by the slow sloping downward curve as opposed to the relatively steep downward curve of intravenous administration.

Figure 1A:
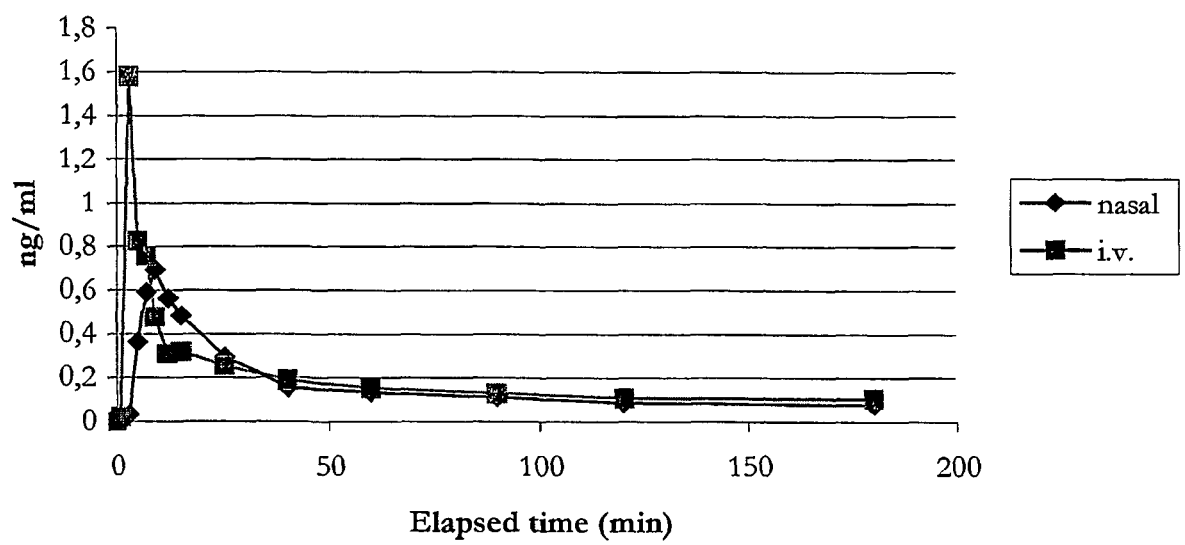
Figure 1B:
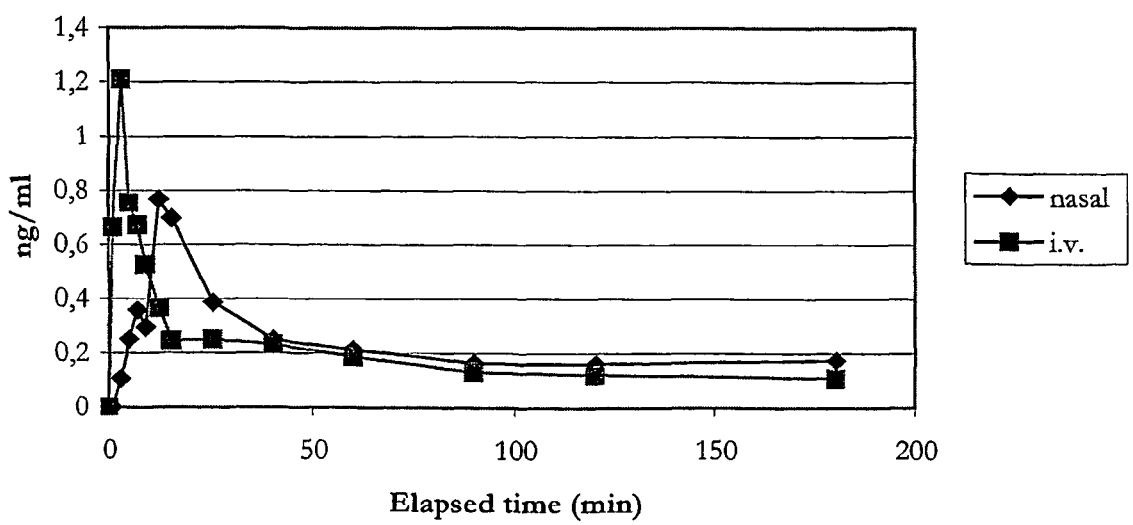
Figure 1C:
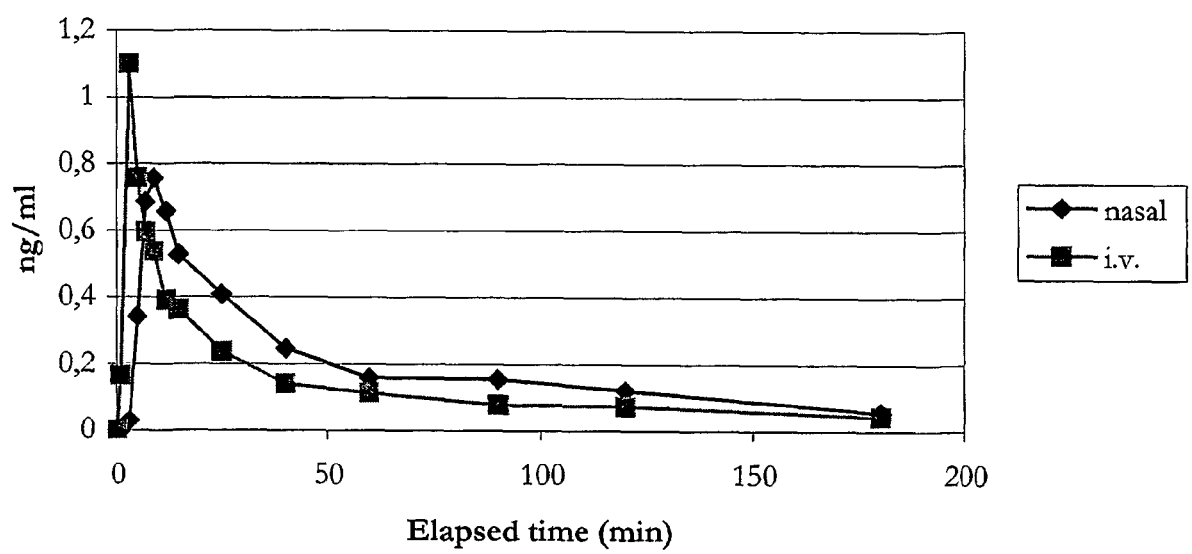
Figure 2A:
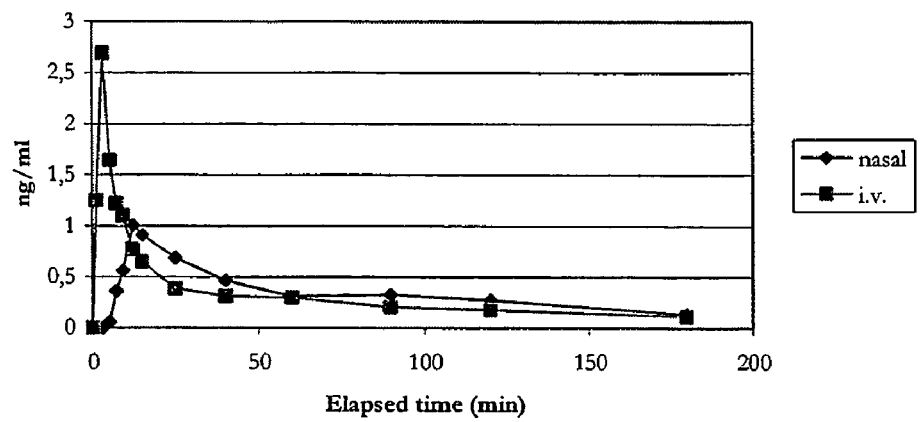
Figure 2B:
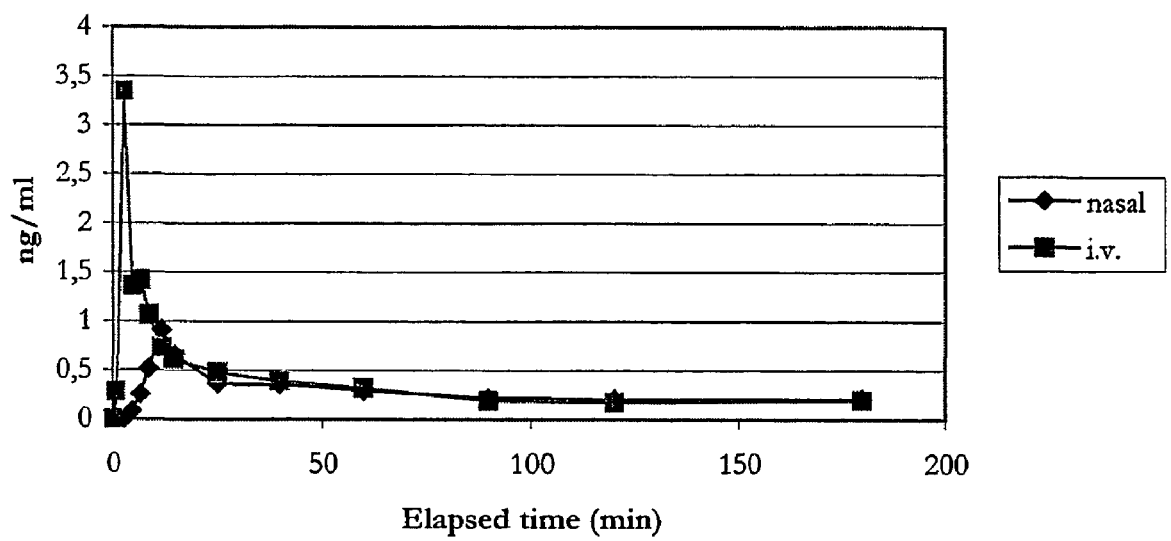
Figure 2C:
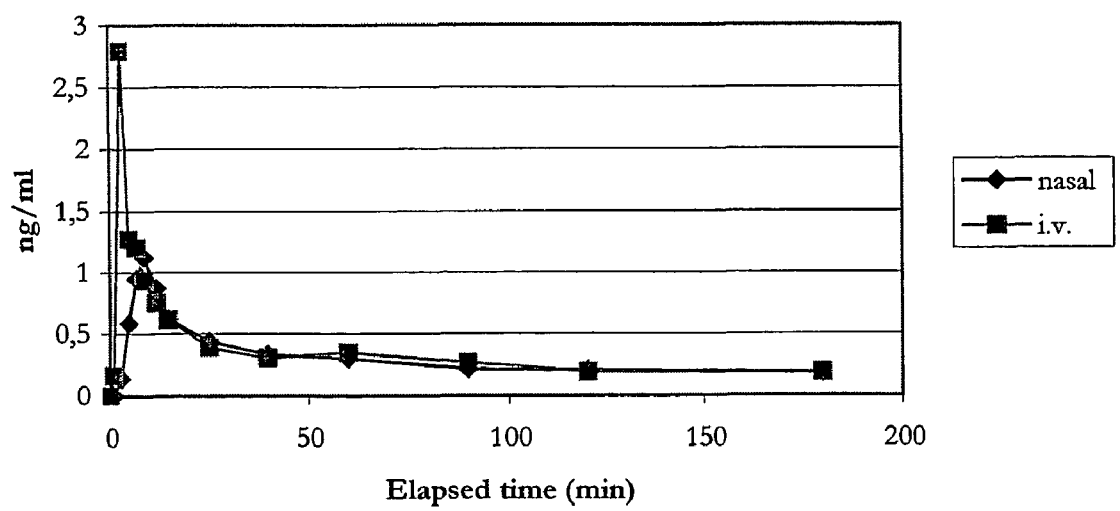
Figure 2D:
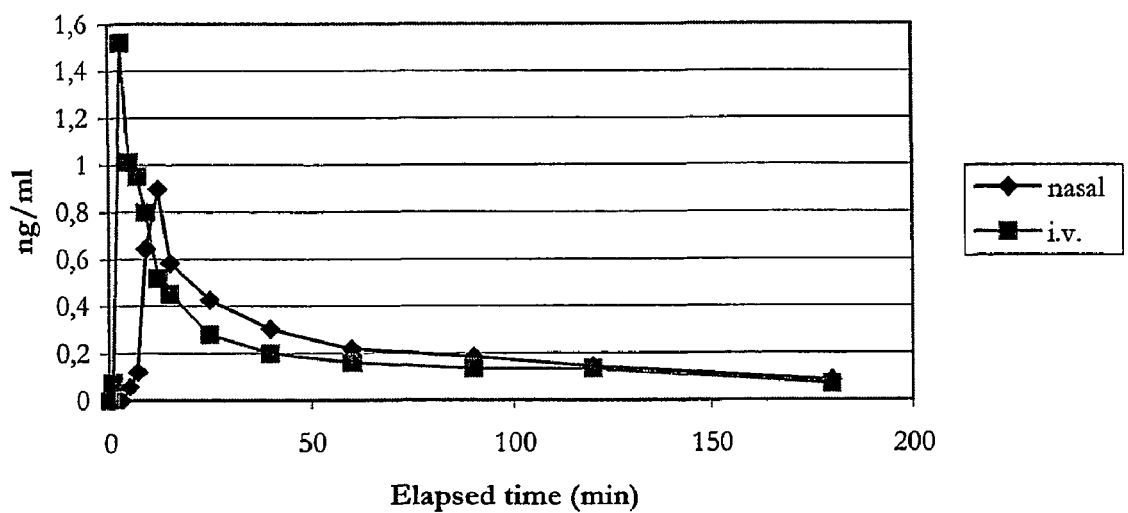

FIGS. 1A, 1B and 1C compare the plasma concentrations of illustrative subjects undergoing treatment with 75 μg of fentanyl by means of nasal administration to those receiving 75 μg of fentanyl by means of intravenous administration. High plasma concentrations are reached relatively rapidly by nasal administration with a longer duration of action. Peak plasma concentrations are lower than by intravenous administration.

FIGS. 2A, 2B, 2C and 2D compare the plasma concentrations of illustrative patients undergoing treatment with 100 μg of fentanyl by means of nasal administration to those receiving 100 μg of fentanyl by means of intravenous administration. High plasma concentrations are reached relatively rapidly by nasal administration with a longer duration of action. Peak plasma concentrations are lower than by intravenous administration.

Figure 3A:
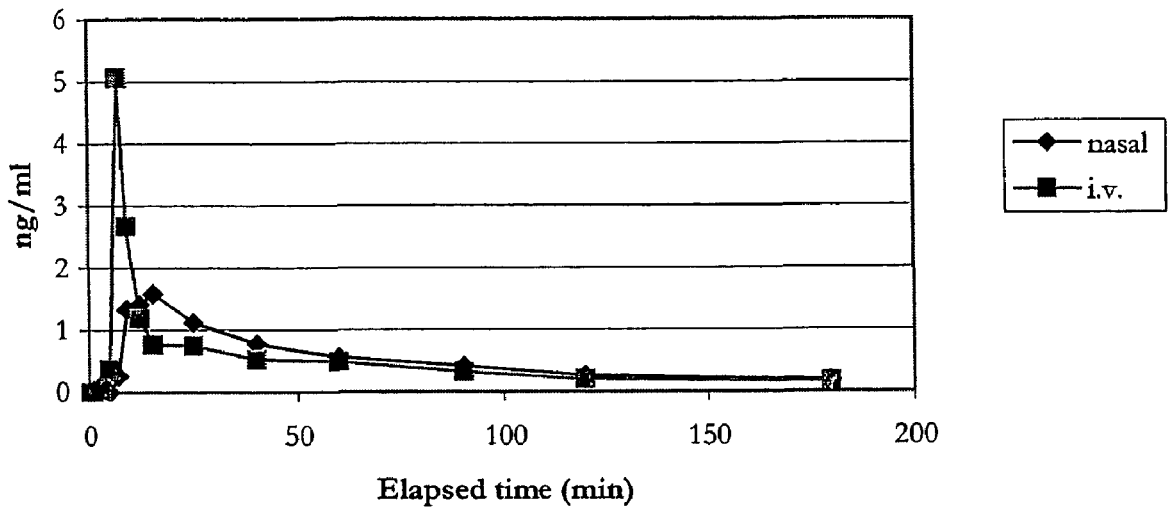
Figure 3B:
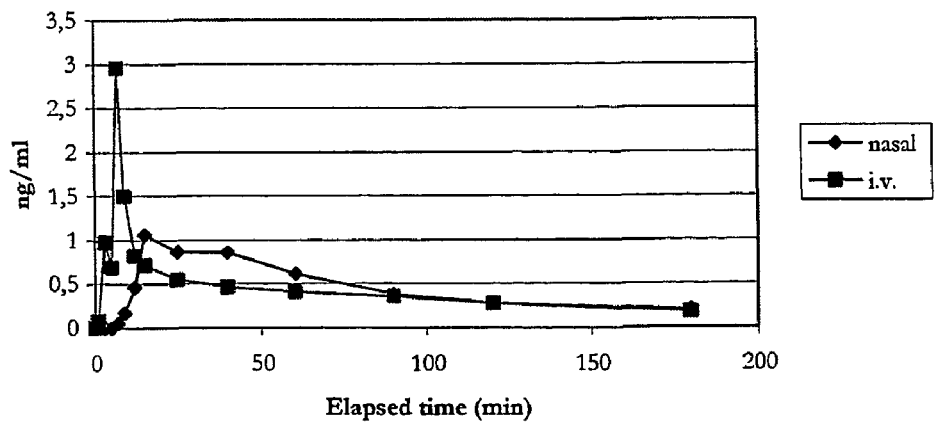
Figure 3C:
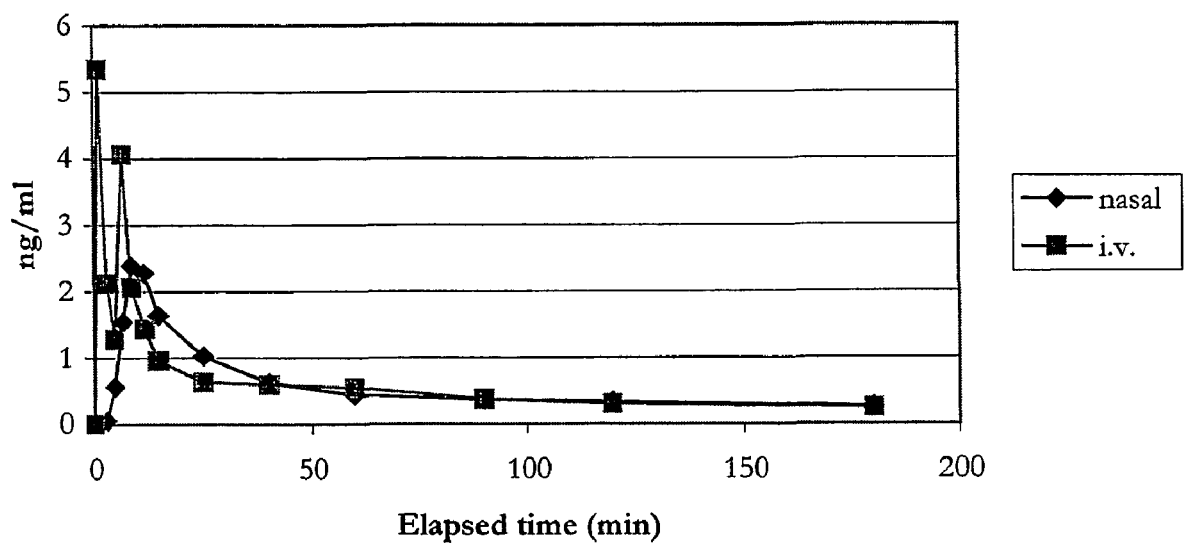

In FIGS. 3A, 3B and 3C compare the plasma concentrations of illustrative patients undergoing treatment with 150 μg of fentanyl by means of nasal administration to those receiving 150 μg of fentanyl by means of intravenous administration. High plasma concentrations are reached relatively rapidly by nasal administration with a longer duration of action. Peak plasma concentrations are lower than by intravenous administration.

Figure 4A:
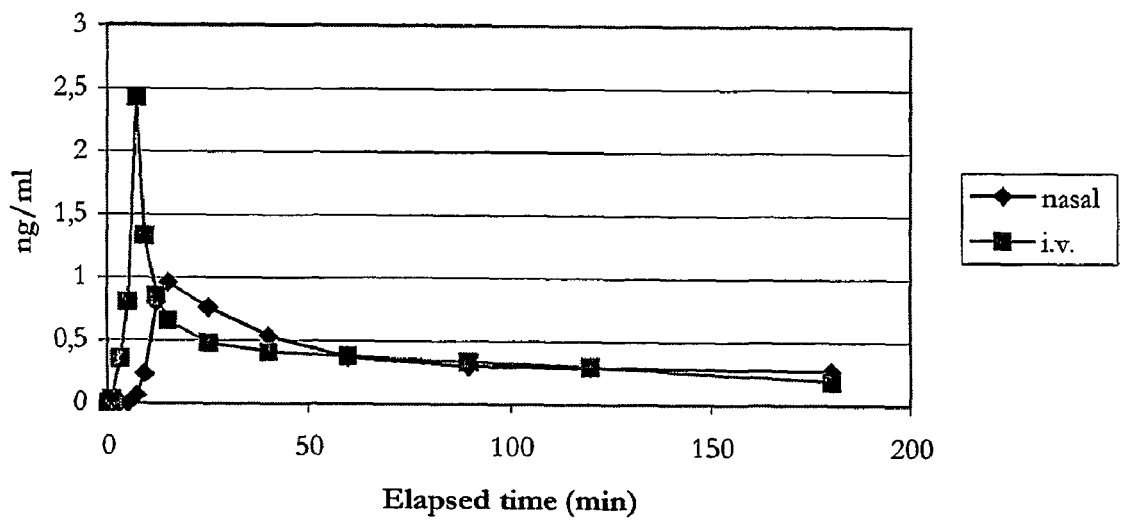
Figure 4B:
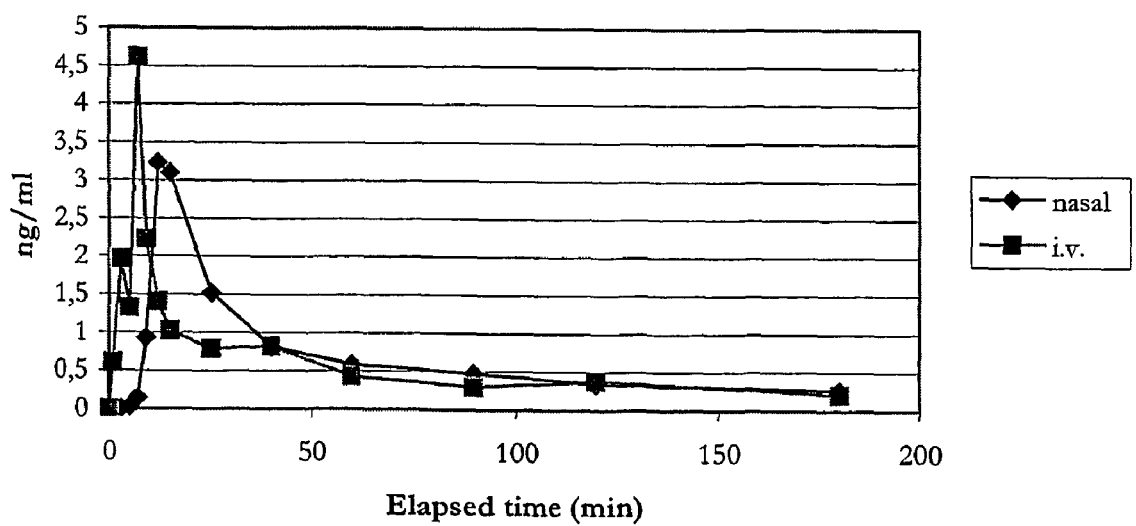

FIGS. 4A, 4B and 4C compare the plasma concentrations of illustrative patients undergoing treatment with 200 μg of fentanyl by means of nasal administration to those receiving 200 μg of fentanyl by means of intravenous administration. High plasma concentrations are reached relatively rapidly by nasal administration with a longer duration of action. Peak plasma concentrations are lower than by intravenous administration.

Figure 5:
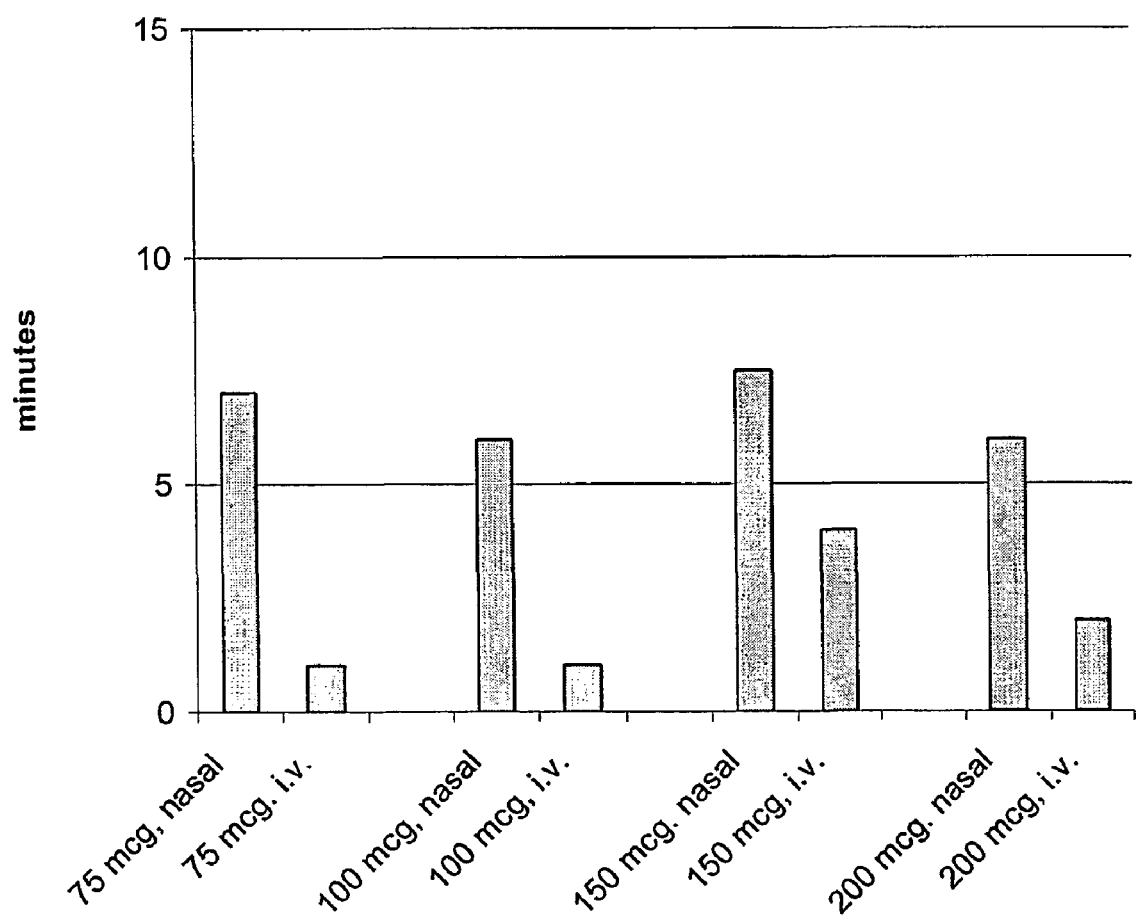
Figure 6A:
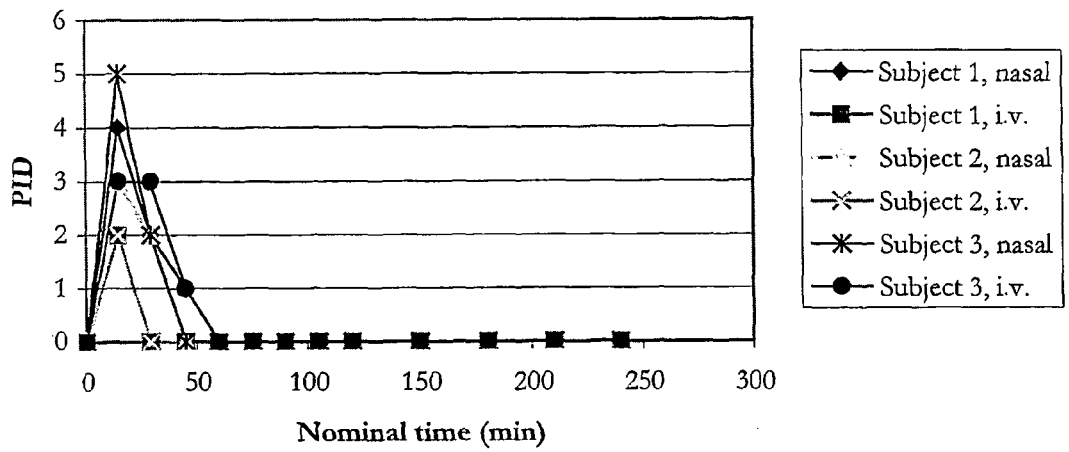
Figure 6B:
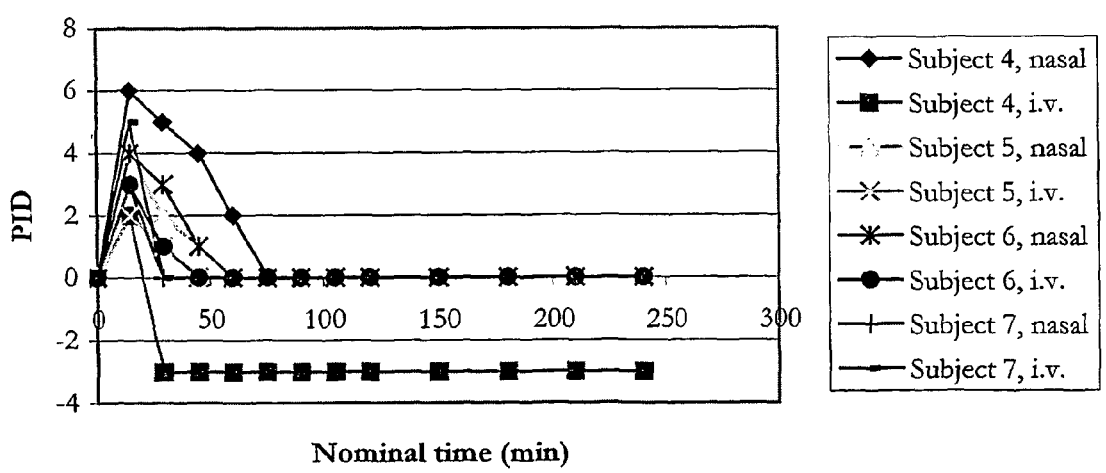
Figure 6C:
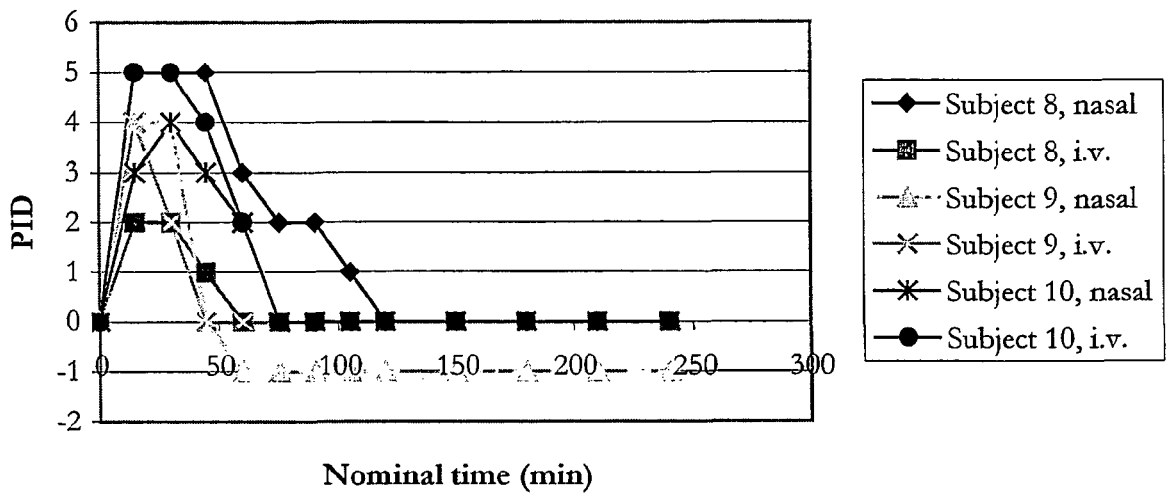
Figure 6D:
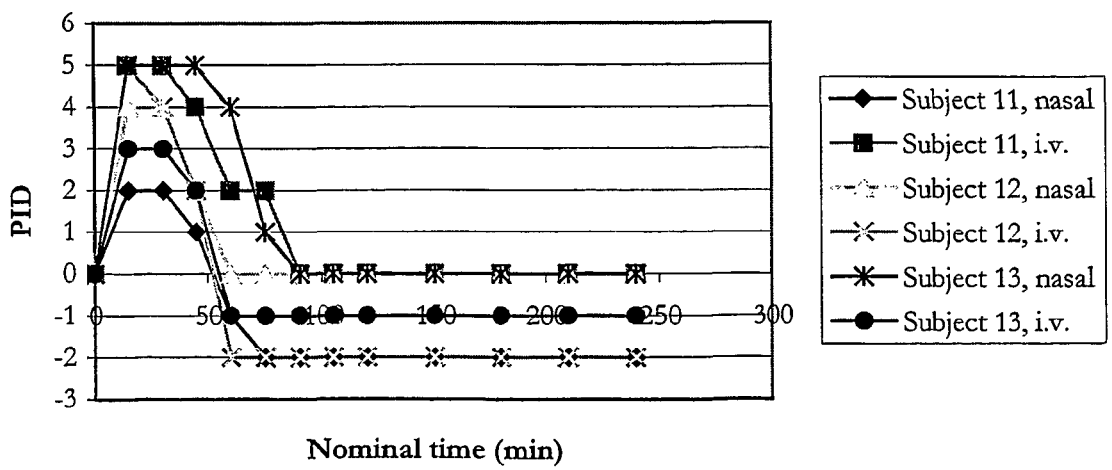

FIG. 5 graphically illustrates the median time to onset of action for the varying doses of fentanyl administered intranasally and intravenously.

FIGS. 6a, 6b, 6c and 6d depict the PID profiles of individual patients at 75, 100, 150 and 200 μg of fentanyl, respectively, administered intranasally in comparison to the same dose administered intravenously.

Figure 7:
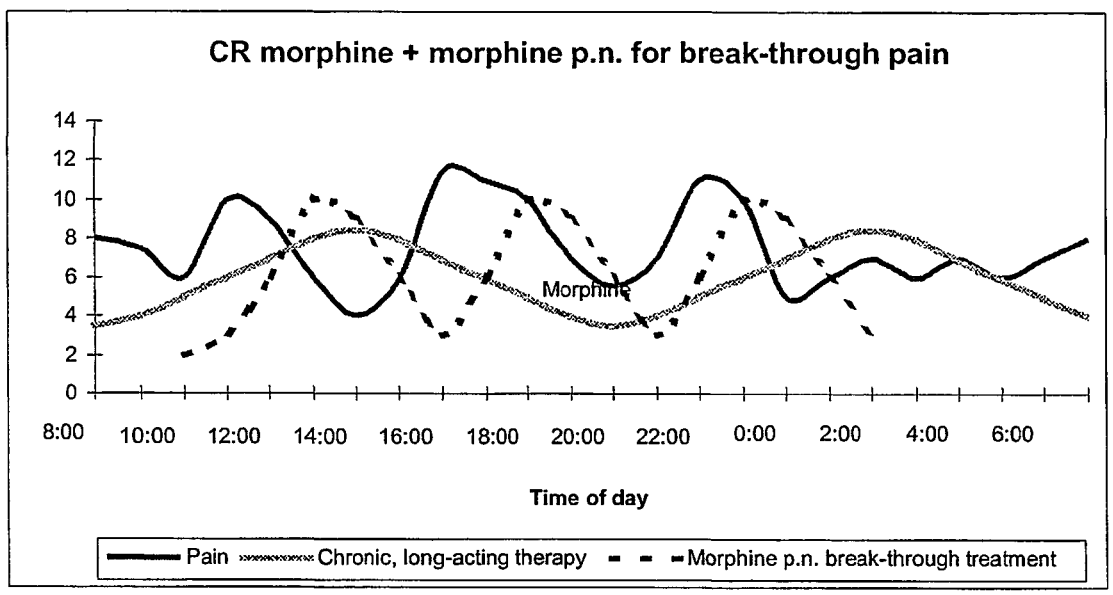

FIG. 7 illustrates the analgesic profile of oral p.n. treatment of breakthrough pain, depicting the typical pain level during the day for a patient. It also shows the coverage in pain alleviation from the long acting, controlled release morphine twice a day and the fast acting p.n. morphine. As illustrated in FIG. 7, it is obvious that the action of the p.n. morphine is too slow to cover the fast occurring breakthrough pain.

Figure 8:
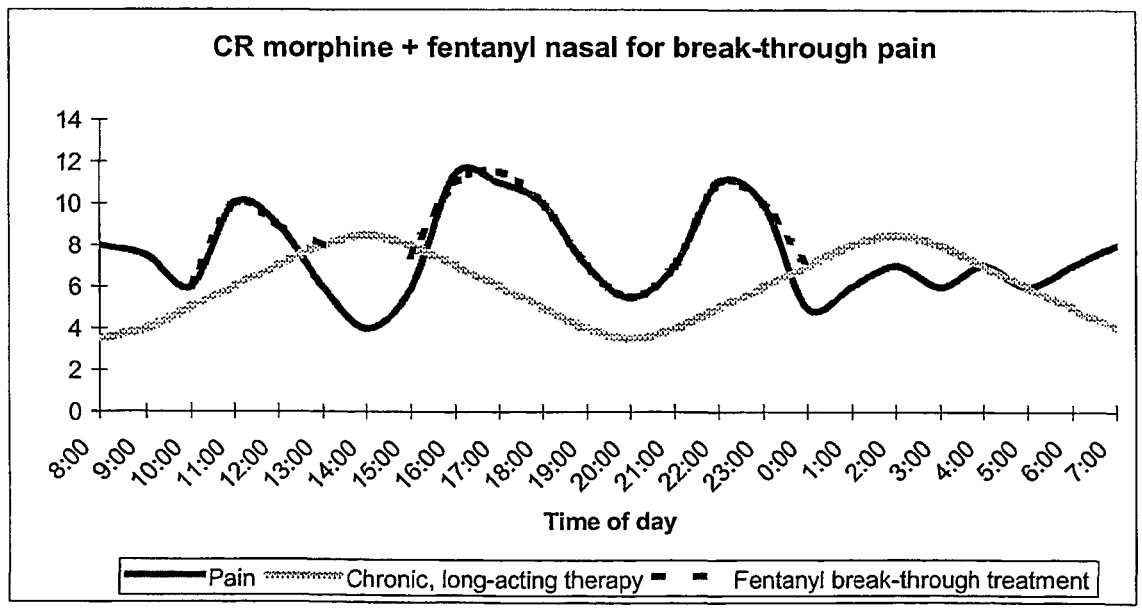

FIG. 8 illustrates the pain relief obtained by the administration of a nasal formulation of fentanyl along with controlled release morphine. The morphine covers the baseline (chronic) pain, whereas the fast onset-of-action of the intranasal fentanyl provides improved pain relief during the breakthrough pain episodes.

EXAMPLES

Example 1

Fentanyl Nasal Formulations, Compositions

Example 1.0

| | | |
|---|---|---|
| I | fentanyl | 0.75 mg to 15 mg |
| II | sodium chloride | 0 to 9 mg |
| III | disodium edetate | 0 to 4 mg |
| | disodium hydrogen phosphate dihydrate | 0 to 15 mg |
| | sodium dihydrogen phosphate dihydrate | 0 to 15 mg |
| IV | purified or sterile water up to | 1 mL |

Fentanyl may be included in the formulation as a salt, appropriately adjusted by weight to achieve the correct concentration of fentanyl. Other tonicity-adjusting agents may be used instead of or in combination with sodium chloride such as dextrose, glycerol, sorbitol, mannitol, potassium nitrate and sodium sulphate decahydrate or mixtures thereof. pH may be adjusted to an appropriate level by use of acids and bases such as hydrochloric acid and sodium hydroxide. Other buffer salts than the phosphates may be used alone or in combination: citric acid, citrate salts and potassium salts. Sufficient microbiological preservation may be achieved by addition of benzalconium chloride, sodium edetate, disodium edetate, benzyl alcohol, parabenes or a combination thereof. Preparation:

The solid ingredients are dissolved one by one or all at the same time in water. The formulation is subsequently filled into appropriate multiple dose or single dose nasal spray devices, which may be equipped with electronic or mechanical recording and/or lock-out systems.

Example 1.1

Composition of fentanyl nasal solution 0.75 mg/ml (75 μg/dose)

| | | |
|---|---|---|
| I | fentanyl citrate | 1.18 mg |
| II | sodium chloride | 7.47 mg |
| II | disodium hydrogen phosphate dihydrate | 2 mg |
| | sodium dihydrogen phosphate dihydrate | 2 mg |
| IV | sterile water | up to 1 mL |

Example 1.2

Composition of fentanyl nasal solution 2 mg/mL (200 μg/dose)

| | | |
|---|---|---|
| I | fentanyl citrate | 3.14 mg |
| II | sodium chloride | 7.37 mg |
| III | disodium hydrogen phosphate dihydrate | 2 mg |
| | sodium dihydrogen phosphate dihydrate | 2 mg |
| IV | sterile water | up to 1 mL |

Example 1.3

Composition of fentanyl nasal solution 4 mg/mL (400 μg/dose)

| | | |
|---|---|---|
| I | fentanyl citrate | 6.28 mg |
| II | sodium chloride | 7.21 mg |
| III | disodium hydrogen phosphate dihydrate | 2 mg |
| | sodium dihydrogen phosphate dihydrate | 2 mg |
| IV | sterile water | up to 1 mL |

Example 1.4

Composition of fentanyl nasal solution 8 mg/mL (800 μg/dose)

| | | |
|---|---|---|
| I | fentanyl citrate | 12.56 mg |
| II | sodium chloride | 6.89 mg |
| III | disodium hydrogen phosphate dihydrate | 2 mg |
| | sodium dihydrogen phosphate dihydrate | 2 mg |
| IV | sterile water | up to 1 mL |

Example 1.5

Composition of fentanyl nasal solution 10 mg/mL (1000 μg/dose)

| | | |
|---|---|---|
| I | fentanyl citrate | 15.70 mg |
| II | disodium hydrogen phosphate dihydrate | 2 mg |
| | sodium dihydrogen phosphate dihydrate | 2 mg |
| III | sterile water | up to 1 mL |

Example 2

Fentanyl Nasal Formulations and Compositions

Example 2.0

| Composition | | |
|---|---|---|
| I | fentanyl | 0.75 mg to 15 mg |
| II | sodium chloride | 0 to 9 mg |
| III | disodium edetate | 0 to 4 mg |
| | disodium hydrogen phosphate dihydrate | 0 to 4 mg |
| | sodium dihydrogen phosphate dihydrate | 0 to 4 mg |
| IV | polyethylene glycol | 1 to 300 mg |
| V | purified or sterile water | up to 1 mL |

Fentanyl may be included in the formulation as a salt, appropriately adjusted by weight to achieve the correct concentration of fentanyl. Other tonicity-adjusting agents may be used instead of or in combination with sodium chloride such as dextrose, glycerol, sorbitol, mannitol, potassium nitrate and sodium sulphate decahydrate or mixtures thereof. pH may be adjusted to an appropriate level by use of acids and bases such as hydrochloric acid and sodium hydroxide. Other buffer salts than the phosphates may be used alone or in combination: citric acid, citrate salts and potassium salts.

To inhibit or reduce adsorption of fentanyl to polymer materials used in the nasal spray device, excipients other than polyethylene glycols (PEG) may be added. Examples of such agents are alcohol, glycofurol, poloxamers, polyoxythylene castor oil derivatives, polysorbates, propylene glycol cyclodextrins, phospholipids and bile salts.

Sufficient microbiological preservation may be achieved by addition of benzalconium chloride, sodium edetate, disodium edetate, benzyl alcohol or parabenes.

Preparation:

The solid ingredients are dissolved one by one in a mixture of IV and V. The formulation is subsequently filled into appropriate multiple dose or single dose nasal spray devices, which may be equipped with electronic recording and/or lock-out systems.

Example 2.1

Composition of fentanyl nasal solution 0.75 mg/mL (75 µg/dose) with 0.1% PEG

| | | |
|---|---|---|
| I | fentanyl citrate | 1.18 mg |
| II | sodium chloride | 7.34 mg |
| III | disodium hydrogen phosphate dihydrate | 2 mg |
| | sodium dihydrogen phosphate dihydrate | 2 mg |
| IV | polyethylene glycol | 1 mg |
| V | purified or sterile water | up to 1 mL |

Example 2.2

Composition of fentanyl nasal solution 0.75 mg/mL (75 µg/dose) with 5% PEG

| | | |
|---|---|---|
| I | fentanyl citrate | 1.18 mg |
| II | sodium chloride | 2.5 mg |
| III | disodium hydrogen phosphate dihydrate | 2 mg |
| | sodium dihydrogen phosphate dihydrate | 2 mg |
| IV | polyethylene glycol | 50 mg |
| V | purified or sterile water | up to 1 mL |

Example 2.3

Composition of fentanyl nasal solution 0.75 mg/mL (75 µg/dose) with 10% PEG

| | | |
|---|---|---|
| I | fentanyl citrate | 1.18 mg |
| II | disodium hydrogen phosphate dihydrate | 2 mg |
| | sodium dihydrogen phosphate dihydrate | 2 mg |
| III | polyethylene glycol | 100 mg |
| IV | purified or sterile water | up to 1 mL |

Example 2.4

Composition of fentanyl nasal solution 0.75 mg/mL (75 µg/dose) with 30% PEG

| | | |
|---|---|---|
| I | fentanyl citrate | 1.18 mg |
| II | disodium hydrogen phosphate dihydrate | 2 mg |
| | sodium dihydrogen phosphate dihydrate | 2 mg |
| III | polyethylene glycol | 300 mg |
| IV | purified or sterile water up to | 1 mL |

Example 2.5

Composition of fentanyl nasal solution 10 mg/mL (1000 µg/dose) with 5% PEG

| | | |
|---|---|---|
| I | fentanyl citrate | 15.70 mg |
| II | sodium chloride | 0.23 mg |
| III | disodium hydrogen phosphate dihydrate | 2 mg |
| | sodium dihydrogen phosphate dihydrate | 2 mg |
| IV | polyethylene glycol | 50 mg |
| V | purified or sterile water | up to 1 mL |

Example 3

Nasal Absorption of Fentanyl in Rabbits

| Formulations | |
|---|---|
| For intravenous administration | 250 µg fentanyl citrate/ml 0.9% saline |
| I for nasal administration | 4 mg fentanyl citrate/ml 0.9% saline |
| II for nasal administration | 4 mg fentanyl citrate/ml 5% PEG300 |
| III for nasal administration | 4 mg fentanyl citrate/ml 30% PEG300 |

Study Design

The above-mentioned formulations were administered to New Zealand white rabbits (n=7) in a cross-over design. The animals were dosed intravenously with a volume of 400 µl (equal to 100 µg fentanyl citrate) injected in a marginal ear vein. Intranasal administration was performed by use of a pipette delivering a volume of 25 µl (equal to 100 µg fentanyl citrate) into one nostril. Blood samples of 500 µl were withdrawn at predetermined time intervals up to 60 minutes. The samples were subsequently centrifuged and the plasma isolated and frozen. The content of fentanyl in the plasma samples was then determined by use of a radioimmunoassay.

Calculations

The area under the plasma concentration-time curve from 0 to 60 minutes (AUC) was determined for all formulations. For each nasal formulation, the bioavailability was calculated using equation 1:

$$\text{Bioavailabilty} = \frac{AUC_{nasal}}{AUC_{intravenous}} \cdot 100\%. \qquad \text{Equation 1}$$

The time for the peak plasma concentrations to occur ($t_{max}$) was determined by visual inspection of the plasma concentration-time curves.

Results

The mean plasma concentration time profiles for the intravenous formulations and the nasal formulations were measured and the overall pharmacokinetic results obtained are given in the table below.

Mean plasma concentration-time profiles of 100 μg of fentanyl citrate administered intravenously and intranasally were in formulations of 0.9% saline, 5% PEG300 and 30% PEG300 (n=7).

In the table below, the bioavailability (F) and time for peak plasma concentrations ($t_{max}$) for intranasal administration of three different formulations of fentanyl (n=7) are shown.

| Range | Formulation I | Formulation II | Formulation III |
|---|---|---|---|
| F (%) | 45-80 | 53-80 | 43-80 |
| $t_{max}$ (minutes) | 2-5 | 2-5 | 2-5 |

Example 4

Protocol for Clinical Trial according to the Present Invention:

A pilot, cross-over study to evaluate the tolerability, pharmacokinetic profile, as well as onset, duration and extent of pain relief of two different formulations of fentanyl in patients with post operative pain after oral surgery.

Trial Phase: Phase II (Therapeutic Exploratory)

Objectives:

The objectives of this study are to establish the tolerability, the pharmacokinetic profile, the onset and duration, and extent of pain relief of intra-nasal application of fentanyl compared to intravenous administration at four different doses.

Trial Design:

This study is designed as a controlled, double blind, double dummy, 2-way crossover study. The patients are randomised to 4 different dose levels (obtained through 2 different formulations) in a balanced way.

Trial Population:

Patients of both genders, age 18 to 40 years, weight normal, with indication for having both mandibular third molars surgically removed.

Assessments:

Baseline Pain Intensity

The baseline pain must be at least "5" on the 11-point numeric rating scale (NRS) to include the patient.

Pharmacokinetic Assessments

Blood samples will be drawn at (0, 1, 3, 5, 7, 9, 12, 15, 25, 40, 60, 90, 120, 180) minutes after administration of study medication.

Pharmacokinetic assessments will be made founded on the results from analysis of fentanyl concentrations in blood samples.

Pain Intensity

Pain intensity will be scored on the 11-point numeric rating scale (NRS). Pain intensity difference and sum of pain intensity difference will be estimated.

Onset and Duration of Analgesic Effect

Onset, duration and time to rescue medication will be measured to obtain evidence of the suitability of fentanyl as treatment for break-through pain.

General Impression

General impression after each period will be obtained.

Tolerability of the Test Drugs

Nasal tolerability, CNS effects, influence on mental state, and peripheral oxygen saturation will be measured.

Investigational Drug:

75 μg fentanyl per dose (blow) and 100 μg fentanyl per dose (blow) for intra-nasal application.

Four dose levels of fentanyl will be administered: 75 μg, 100 μg, 150 μg (75 μg×2, five minutes interval between doses), 200 μg (100 μg×2, five minutes interval between doses).

Comparator:

Intravenous 75 μg Fentanyl, and Intravenous 100 μg Fentanyl.

Four dose levels of fentanyl will be administered intravenously: 75 μg, 100 μg, 150 μg (75 μg×2, five minutes interval between doses), 200 μg (100 μg×2, five minutes interval between doses).

Placebo:

To achieve the blinding a nasal application of isotonic buffered saline and an i.v. sterile water will be used.

Trial Visit Procedures

|  | Screening/ Inclusion Day | First Operation Day | First Control Visit | Second Operation Day | Second Control visit |
|---|---|---|---|---|---|
| Informed Consent | x | | | | |
| Inclusion/ Exclusion Criteria's | x | x | X | x | x |
| Physical Examination | x | | | | |
| Past and Concomitant Illness | x | x | X | x | x |
| Urine sample for screening for drug abuse | | x | | x | |
| Urine sample for screening for pregnancy | | x | | x | |
| Blood samples for pharmakokinetic analysis | | x | | x | |
| Data on Pain | | x | | x | |
| Oxygen Saturation | | x | | x | |
| Tolerability | | x | | x | |
| Adverse Events | | x | | x | |

| List of abbreviations and definitions of terms used in the protocol | |
|---|---|
| AE: | Adverse event |
| CRF: | Case Report Form |
| SAE: | Serious Adverse Event |
| GCP: | Good Clinical Practice |
| ITT: | Intention-to-treat |
| PP: | Per-protocol |
| NRS: | Numeric rating scale |
| IMAFT: | fentanyl |
| CI: | Confidence interval |
| PI: | Pain intensity |
| PID: | Pain intensity difference |
| SPID: | Sum of pain intensity difference |
| AUC: | Area under the curve |
| $C_{max}$: | Peak plasma concentration |
| $T_{max}$: | Time when peak plasma concentration is obtained |
| $k_e$: | Elimination rate constant |
| MRT: | Mean residence time |
| HVD: | Half value duration |
| $T_{\geq 75\% Cmax}$: | Duration of plasma concentration above 75% of $C_{max}$ |

At present, fentanyl is administered as i.v., i.m., transdermal or buccal formulations. This study is designed to investigate the pharmacokinetic, tolerability and pain relieving aspects of intra-nasal application of fentanyl. The intra-nasal administration of fentanyl will be non-invasive and should provide a rapid way of pain relief.

The term break-through pain generally refers to transitory exacerbation of pain that occurs on background of otherwise stable pain in a patient receiving chronic analgesic treatment such as with an opioid treatment. The golden standard for treating episodes of break-through pain has for many decades been supplementary p.n. doses of short acting oral morphine. The nature of cancer pain being dynamic necessitates adjustment of the dose level of chronic, long-acting opioid according to the level of p.n. morphine and the intensity and duration of pain episodes.

The analgesic profile of plain morphine tablets for p.n. use comprise an onset of analgesia within ½-1 hour, a peak effect after 1½-2 hours and a duration of effect of 4-6 hours. Optimising the treatment of break-through pain must focus on a very fast onset of action, a powerful and flexible pain relief and a sufficiently short duration to cover only the break-through episode, and thereby minimising side effects.

The analgesic profile of oral p.n. treatment of break through pain is illustrated by the following drawing of FIG. 7, where the typical pain level during the day for a patient is illustrated together with an illustration of the pain control treatment divided in the coverage from the long acting, controlled release morphine twice a day, and the fast acting p.n. morphine. As illustrated in FIG. 7 it is obvious that the action of the p.n. morphine is too slow to cover the fast occurring break-through pain.

Recently, transdermal fentanyl in a patch formulation (Durogesic®) has gained increasingly popularity due to the ease of use and a tendency towards better tolerability. The use of fentanyl as basic, long-acting pain treatment in cancer patients calls for the use of the same generic in a formulation designed to cover break-through pain episodes.

By a nasal formulation of fentanyl as illustrated in FIG. 8, many of the features to gain successful treatment of break-through pain is obtained: a very fast onset of action—around 5 minutes—and a flexibility due to the possibility of divided doses securing a sufficient dosage of analgesia reflecting the need both with respect to intensity and to duration.

The development of the nasal fentanyl is aiming at treating, for one, cancer patients. This pilot study to confirm the concept is extendable to cancer patients, despite directed in this study to patients in need of analgesic treatment due to pain after oral surgery. The Third molar surgery model has the advantage of being a homogeneous pain model due to the uniformity of patients, procedures, operative trauma and therefore predictable and stable level of pain without confusing 'noise' from the many factors normally influencing the pain and wellbeing of cancer patients.

The dose schedule used in this study is first of all based on the recommendations for i.v./i.m. fentanyl for postoperative pain: 50 to 100 µg, repeated to achieve the desired level of analgesia—and secondly on the published pharmacokinetics of nasal fentanyl with a bioavailability of the nasal application of 71% as compared to i.v. fentanyl (9). Also the experience from acute pain treatment in the anaesthesiologist-staffed ambulance service 'Laegeambulancen' where fentanyl for more than 5 years has been the drug of choice for pain treatment in starting doses of 100 µg i.v. repeated with 5 to 10 minutes intervals until desired effect. In this setting, doses of up to 400 µg are given to patients suffering from very severe pain. The tolerability of this regimen has, retrospectively, been checked in hospital records to document the safe use (10).

Tolerability, onset-of-action and duration-of-action were assessed by a dose finding approach starting with a low dose of 75 µg and a medium dose of 100 µg. Investigating higher dose levels is achieved by repeating the dose with a interval of five minutes, thereby obtaining the desired fast onset, and in addition a sufficient duration of action (designed to manage the break-through pain episodes of ½-1 hour), but avoiding too high a peak plasma concentration.

A cross-over design is applied to gain bioavailability data. The treatment dosages were 75 µg single dose, 75 µg dual dose, 100 µg single dose and 100 µg dual dose.

Because fentanyl is a narcotic analgesic drug, patients—not healthy volunteers—have been chosen as trial subjects.

Objectives

The objectives of this study are to establish the tolerability, the pharmacokinetic profile, the onset, duration, and extent of pain relief of intra-nasal application of fentanyl compared to i.v. administration at four different doses.

Trial Design

This study is designed as a controlled, double-blind, double dummy, 2 way cross-over study. The patients were randomised to 4 different dose levels and 2 formulations in a balanced way.

Postoperative Procedures

The patients are asked not to leave the department. If the patient does not experience pain intensity of at least "5" on the 11-point NRS within 4 hours, the patient did not receive study In a cross over study where the patient receive the same dose but in different formulation in each of two periods, the patients serve as his/her own control—in this case supplying a good calculation of the bioavailability and pharmacokinetic data and comparable pain scores. The study is double-blind in order to obtain objective pain scores.

Methods and Assessments/Measurements

Patients experiencing pain intensity of at least "5" at the 11-point NRS within 4 hours received study medication (and if necessary rescue medication). These patients were asked to stay for another four hours for safety reasons and in order to observe onset and duration of pain relief and to fill-in the questionnaire part of the CRF regarding the effect of the study medication. Recordings of pain intensity, tolerability of the study drug, and oxygen saturation were performed at the following time points:

before intake of study drug (time=0)

every 15 minutes after intake of study drug for the first 2 hours every 30 minutes for the last 2 hours of the stay at the department.

Simultaneously blood samples were obtained for pharmacokinetic studies (0, 1, 3, 5, 7, 9, 12, 15, 25, 40, 60, 90, 120, 180) minutes after administration of study medication.

Overview of post-operative sampling and recordings:

| Time after administration/ minutes | Blood sample | Pain intensity | Tolerability | Oxygen saturation |
|---|---|---|---|---|
| 0 | X | X | X | X |
| 1 | X | | | |
| 3 | X | | | |
| 5 | X | | | |
| 7 | X | | | |
| 9 | X | | | |
| 12 | X | | | |
| 15 | X | X | X | X |
| 25 | X | | | |
| 30 | | X | X | X |
| 40 | X | | | |
| 45 | | X | X | X |
| 60 | X | X | X | X |
| 75 | | X | X | X |
| 90 | X | X | X | X |

-continued

| Time after administration/ minutes | Blood sample | Pain intensity | Tolerability | Oxygen saturation |
|---|---|---|---|---|
| 105 | | X | X | X |
| 120 | X | X | X | X |
| 150 | | X | X | X |
| 180 | X | X | X | X |
| 210 | | X | X | X |
| 240 | | X | X | X |

The patient was provided with 2 stopwatches. Both watches were started in connection with the administration of study medication. One watch was stopped when the patients are certain of the effect of the study drug, and the second when the patients experience recurrence of pain. Pain recurrence is defined as "pain relief is no longer meaningful". If patients took rescue medication before stopping the second stopwatch, the time until rescue medication was used as "time to effect-end". The times for "onset-of-action" and "effect-end" were recorded in the CRF. The time for administrating study medication is recorded in the CRF. If the study medicine did not give sufficient pain relief the patient is allowed to take rescue medicine (Ibumetin®, Nycomed Danmark) 600 mg, 10 pcs.). The patient was asked to wait at least 1 hour before taking the extra medicine, if possible. The patient was allowed to bring the rescue medicine home, and was asked to bring the remaining rescue medication and/or the empty package back at the control visit. At the end of the observation period the patient scored the general impression of the treatment.

The questionnaire part covers time from intake of trial medication and the next 4 hours. During the stay at the department, recordings of adverse events, if any, took place First Control Visit One week after the operation the patient returns for a control visit. Intake of rescue and concomitant medication, as well as adverse events, spontaneous reported and reported after direct questioning, if any, are recorded in the CRF.

Second Operation Day

At least one week after the controls visit a second operation is performed. The procedure from $1^{st}$ operative day is repeated.

Postoperative Procedures

The procedure from $1^{st}$ operative day is repeated except that patients were treated with the test drug if they need pain relief, also if their pain intensity does not reach "5" at the 11-point NRS scale.

Second Control Visit

One week after the second operation the patient returns for a control visit. The procedures are identical to first control visit.

Administration and Dosage

The study medicine must be taken when the patient experiences moderate to severe pain after the oral surgery (pain intensity of "5" or more on the 11-point NRS). The patient received both formulations to achieve the double blind design of the study. Each patient therefore has two nasal applications—one in each nostril—with an interval of five minutes. Simultaneously, the patients have two i.v. injections of 2.0 mL with an interval of five minutes. At least the first dose of test medicine will, depending on randomization, be either fentanyl intranasal or fentanyl intravenous. The placebo intranasal and intravenous is used as second dose for the two lowest dosage groups.

Baseline Pain Intensity

The baseline pain must be at least "5" on the 11-point numeric rating scale (NRS) to include the patient.

Question: "Please tick off the pain intensity on the 11-point scale where 0 corresponds to "no pain", and 10 corresponds to "unendurable pain"

The investigator or nurse enters the times and date of intake of medicine in the CRF.

Pharmacokinetic Assessments

Blood samples of maximal 4 mL were drawn at the above specified time points (a total of 14 samples, corresponding to maximal 56 mL). Samples were centrifuged under cooling conditions at 5° C., plasma was separated and stored at −20° C. Plasma samples were shipped in one batch to the laboratory, adequately packed.

Details on laboratory procedures were described in the Laboratory Analysis protocol. Pharmacokinetic parameters were calculated.

Onset of Analgesic Effect

Time to onset of effect (first stopwatch).

Duration of Analgesic Effect

Offset of analgesic effect (second stopwatch) was stated in the CRF and duration of effect is defined as the length of the interval from onset of effect to offset of effect. However, if the patient requires rescue medication before offset, duration was measured as time from onset to the time of rescue medication.

Pain Intensity (NRS)

Pain intensity is scored on the 11-point NRS scale. Recordings took place every 15 minutes after intake of study drug for the first 2 hours and thereafter every 30 minutes for the last 2 hours stay at the department.

$PI_i$ is the value of Pain Intensity at time point $T_i$ (missing values have been adjusted as described under "Correction of scores").

Pain Intensity Difference (NRS)

$PI_0$ is the baseline value of Pain Intensity (at time point $T_0$).

$PID_i$ is the value of Pain Intensity Difference at time point $T_i$.

$$PI_{Di}=PI_0-PI_i$$

Sum of Pain Intensity Difference, SPID, 4 hours $CPID_i$ is the cumulated (time weighted) sum of PID up to the time point $T_i$.

$$CPID_1=PID_1*(T_1-T_0)$$

$$CPID_2=CPID_1+PID_2*(T_2-T_1)$$

$$CPID_i=CPID_{i-1}+PID_i*(T_i-T_{i-1})$$

$$SPID=CPID_i \text{ for } i=N$$

General Impression (5-Point Scale, 4 Hours)

Four hours after intake of the study medication, or at the time of intake of rescue medication, the patient was asked about his/her general impression of the study drug. This was done on a 5-point VRS as described below.

Question: "What do you think about the study medication?"

Possible answers:

Poor (0); Fair (1); Good (2); Very good (3); and Excellent (4) were stated in the CRFs.

Tolerability of the Test Drugs
    See below.
Adverse Events
    See below.
Correction of Scores
Duration of Analgesia:
    For duration, the observation point for patients who continue to have meaningful effect at the end of the observation period is considered to be censored.
Pain Intensity and Pain Relief:
    Patients who dropout due to lack of effect or who take rescue medication between one and 4 hours after study medication will keep the pain intensity score immediately prior to dropping out/taking rescue medication, or the baseline value depending on which is worse. The pain relief score was recorded as 0.
    This procedure may underestimate the effect of the drugs but imitates the clinical course. If no treatment is given, the patient's pains normally stay the same or increase, and the patient does not experience any relief.
Time to Rescue Medication:
    Patients who do not require rescue medication within 4 hours after study drug administration were considered to have censored observations. Missing data in general impression were set to missing and were therefore not be included in the calculations.
    Concomitant illness relates to any illness that is present at the start of the trial and continues unchanged. Concomitant medication relates to any medication other than the trial product that is taken during the trial, including screening and run-in periods. During the operation local anesthetics (3% Citanest-Octapressin®), Astra) was used. The study medicine was nasal fentanyl wherein two different dose strengths of fentanyl for nasal application were used in the four different treatment groups:
    750 µg/mL (as fentanyl citrate)
        in a single dose nasal spray device produced by Pfeiffer, delivering a single validated dose of 100 µL, corresponding to a dose of 75 µg of fentanyl per dose. Nycomed Pharma performed the manufacturing of the fentanyl solution and filled the devices.
    1 mp/mL (as fentanyl citrate)
        in a single dose nasal spray device produced by Pfeiffer, delivering a single validated dose of 100 µL, corresponding to a dose of 100 µg fentanyl per dose. Nycomed Pharma performed the manufacturing of the fentanyl solution and filled the devices.
Comparative Treatment, Fentanyl i.v.
    One dose strength of fentanyl was used for the comparative double blind formulation to be used for i.v. application:
    Fentanyl solution for injection 50 µg/mL (as fentanyl citrate), Haldid®, ampoules of 2 mL, manufactured by Janssen-Cilag. This solution was diluted with sterile water, Nycomed Pharma, in order to achieve an injection volume of 2 mL in all single injections, meaning that the 100 µg group will be dosed with pure Haldid® and the 75 µg group received 1.5 mL of Haldid® diluted with 0.5 mL sterile water to 2.0 mL injection volume.
Placebo Treatment.
    To achieve the blinding a double dummy technique was applied. Nasal application devices produced by Pfeiffer, filled with isotonic buffered saline was used as dummies. Nycomed Pharma filled the devices. Likewise, sterile water, Nycomed Pharma was used for dummy blinding as the second dose of the i.v. treatment in two of the treatment groups.

Medicine for Analysis
    In order to check shelf-life under trial conditions, 10 nasal delivery devices of each dose strength and 10 ampoules of test drug were stored together with the trial medicine at the site of investigation, and were analysed by Nycomed, after termination of the study. Storage temperature must be below 25° C.
Randomisation and Blinding
    A sealed code with the randomisation number containing information about the treatment for the particular subject will be supplied for each subject.
    The patients were randomised in a balanced way, securing an equal distribution between treatments (intranasal and intravenous) as well as between dosage groups (75 µg, 100 µg, 150 µg, and 200 µg).
    The study was double-blind, that is blinded to the patient, the staff and in addition to the laboratory staff performing the fentanyl analysis, the Data Management and the statistician until analyses are completed. As the patients and staff are blinded to the treatment the schedule must be identical for all patients. This is achieved by a double-dummy blinding technique for the nasal formulation and for the i.v. control as well due to the wish of using an approved and marketed i.v. formulation. The blinding by double-dummy technique can be summarised:

| Dose group | Nasal period* | | I.v. period | |
|---|---|---|---|---|
| | 1. dose | 2. dose | 1. dose | 2. dose |
| 75 µg | fentanyl nasal | Placebo nasal | fentanyl i.v. | Placebo i.v. |
| | Placebo i.v. | Placebo i.v. | Placebo nasal | Placebo nasal |
| 100 µg | fentanyl nasal | Placebo nasal | fentanyl i.v. | Placebo i.v. |
| | Placebo i.v. | Placebo i.v. | Placebo nasal | Placebo nasal |
| 150 µg | fentanyl nasal | fentanyl nasal | fentanyl i.v. | fentanyl i.v. |
| | Placebo i.v. | Placebo i.v. | Placebo nasal | Placebo nasal |
| 200 µg | fentanyl nasal | fentanyl nasal | fentanyl i.v. | fentanyl i.v. |
| | Placebo i.v. | Placebo i.v. | Placebo nasal | Placebo nasal |

*The term Nasal period and i.v. period is used for illustration and does not reflect the order of treatment for patients, this is dependent solely on randomisation.

All i.v. administrations are prepared the same way: 1.5 mL is always taken from "1. Ampoule" and 0.5 mL is always taken from "2. Ampoule". The different doses are achieved as follows:

| | Time "0" dose | | Time "5 minutes" dose | |
|---|---|---|---|---|
| Dose group | 1. Ampoule | 2. Ampoule | 1. Ampoule | 2. Ampoule |
| 75 µg | Haldid® | Sterile water | Sterile water | Sterile water |
| 100 µg | Haldid® | Haldid® | Sterile water | Sterile water |
| 150 µg | Haldid® | Sterile water | Haldid® | Sterile water |
| 200 µg | Haldid® | Haldid® | Haldid® | Haldid® |

All adverse events are classified as either serious or non-serious based on strictly objective definitions.
Tolerability
    Nasal tolerability, signs and symptoms related to CNS effects of fentanyl, and the influence of fentanyl on mental state was recorded separately. Likewise the peripheral oxygen saturation—as an indicator of respiratory depression was recorded. All such signs and symptoms that are considered adverse events must be noted.

Tolerability of the Test Drugs

This trial has a focus on the tolerability of the nasal application form, therefore specific questions related to the nasal application has been included. All recordings obtained in this section must, if they are categorised as adverse events, additionally be recorded as such. Recordings will take place before intake of study drug and every 15 minutes thereafter for 2 hours, then every 30 minutes for the last 2 hours stay at the department.

Nasal Tolerability.

Please score the following effect on an 11-point NRS where 0 corresponds to no effect and 10 to the greatest effect imaginable Sore, itching or stinging nose:
Sore or stinging throat:
Dry or stuffy nose:
Runny nose:
Taste Disturbance:
CNS Effects
    Please score the below effects on an 11-point NRS:
    Sedation: 0 corresponds to absolutely normal, active lively and dynamic and 10 means completely relaxed, calm, peaceful and tranquil
    Nausea: 0 corresponds to perfectly normal, no nausea and 10 means completely sick, about to vomit
Mental State
    Please state the drug influence on mental state by a yes/no answer: Do you feel high?
        Are things around you mere pleasing than usual?
        Is your speech not as loud as usual?
        Do you feel more dreamy than lively?
Oxygen Saturation
    Peripheral oxygen saturation was measured transcutaneous (Pulse oxymetry with UV detection) and recorded every 15 minutes for the first 2 hours post-dose, and thereafter every 30 minutes.

Statistical Considerations

The Trial Statistician was responsible for the statistical analyses. A sample size calculation relating to the pharmacokinetic objective of the trial shows that the suggested number of patients gives a realistic possibility of detecting the expected difference in AUC. The design of the trial includes 2 administration routes and 4 different doses. The power considerations below are based on the assumption of dose-AUC linearity, which allows for joining of the four dose groups. This leads to a comparison of the two administration routes via a paired t-test.

In a previous trial with i.v. administration of fentanyl(ref), an intra patient variability of 29% on the $C_{max}$ parameter was found. Generally it is expected that the variability of $C_{max}$ and AUC are of the same magnitude. In the same study there is a difference of 30% in AUC between nasal and i.v. administration.

Primary Endpoint

The AUC is chosen as the primary endpoint, as the sample size and power calculation justify a result that can detect a difference in AUC between the formulations in the level of what can be expected.

Secondary Endpoints:
Onset of Analgesic Effect.

The distribution function of time to onset of effect was analysed as a time to onset variable using the Kaplan-Meier product limit estimation procedure with the purpose of giving a graphical presentation of time to onset. The mean time to rescue medication and 90% Cl was calculated Duration of Analgesic Effect Median duration of analgesic effect and 90% Cl were calculated.

Time Until Rescue Medication:

The distribution function of time to rescue medication for patients reporting onset of effect were analysed as a time to onset variable using the Kaplan-Meier product limit estimation procedure with the purpose of giving a graphical presentation of tome to onset. The mean time to rescue medication and 90% Cl were calculated The amount of rescue medication used were tabulated.

General impression (5-point scale):

Proportions of patients in the 5 categories were illustrated graphically.

Tolerability of the Test Drugs
    Nasal tolerability (sum of 5 different 11-point scale scorings):
    Results were tabulated and the mean sum and 90% Cl were calculated CNS effects (sum of 2 different 11-point scale scorings):
    Results were tabulated and the mean sum and 90% Cl were calculated Influence on mental state (yes/no response to: feeling high, feeling pleased, feeling of low voice, feeling dreamy):
    Results were tabulated and the mean sum of positive responses and 90% Cl were calculated
    Peripheral oxygen saturation measured transcutaneous:
    Graphical presentation of the mean saturation alone, in combination with plasma concentration of fentanyl, and together with pain relief and intensity scores were presented.

Adverse Events

Because of the exploratory nature of the trial, all comparative analyses were conducted on the Per Protocol population.

Methods of Analysis
Primary Endpoint

The pharmacokinetic profiles of the two application forms were compared by derived variables of fentanyl.

The following variables were calculated:
$AUC_{0-4}$, area under the curve from zero to 4 hours
$C_{max}$, peak plasma concentration
$T_{max}$, time to peak plasma concentration
MRT, mean residence time
HVD half value duration
$T_{\geq 75\%} C_{max}$, duration of plasma concentration above 75% of $C_{max}$ when $K_e$, elimination rate constant AUC and MRT were calculated using the trapezoidal rule and the AUMC method (11, 12). The parameters AUC and $C_{max}$, will be tested for dose linearity. Where linearity can be assumed, the administration routes were compared by a t-test. If not, the comparison takes account of dose.

The following formula were used for the extrapolation, where it is possible to estimate $k_e$ (n denotes the time for the last data point with measurable concentrations):

$$\frac{C_p}{k_e}(AUC), \text{ and } \frac{n \times C_p}{k_e} + \frac{C_p}{k_e^2}(AUMC)$$

If it is not possible to estimate $k_e$ with reasonable precision in the single patient, a common estimate were used, where the results suggest that it is appropriate. Alternatively, the patients were excluded from the analysis of the particular parameter. The elimination rate constant ($k_e$) was determined as the terminal slope of the semi-logarithmic plasma concentration time curve by linear regression.

The peak plasma concentration ($C_{max}$) was the maximum of the measured concentrations and the time to peak concentration ($T_{max}$) the corresponding sample time.

The half value duration (HVD) (13) was the time interval with plasma concentrations above 50% of $C_{max}$, and correspondingly $T_{\geq 75\%} C_{max}$ was the time interval with plasma concentrations above 75% of $C_{max}$ $T_{max}$ was compared between the administration routes via non-parametric methods.

Exploratory analyses is conducted on the pharmacokinetic profiles and on other pharmacokinetic parameters.

Medicine for Analysis:

Will be packed simultaneously with the test medicine, each fentanyl preparation was packed in separate boxes, and was labelled accordingly.

Example 5

5.1 Solubility of Fentanyl Citrate in PEG-Water Mixtures at 25° C.

It was found that the solubility of FC decreased with increasing concentrations of PEGs. However, pH varied from about 4 in 2.5% PEG to about 8 in 100% PEG. The solubility in 0.9% saline was about 16 mg/ml.

Since it was not possible to keep pH at a constant level, it was decided to use a phosphate-citrate buffer (pH 6) for further experiments.

Example 5.2

Solubility of Fentanyl Citrate in PEG-Buffer Mixtures, pH 6 at 25° C. and 8° C.

With pH maintained between 5.9 and 6.5 (and therefore fentanyl citrate almost completely ionised), the solubility of FC decreased from about 27 mg/ml in pure buffer to about 10 mg/ml with 30% PEG at 25° C. At 8° C. the solubility in 2.5% PEG was about 10 mg/ml and in 100% PEG about 3 mg/ml.

Example 5.3

Solubility of Fentanyl Citrate in PEG-Buffer Mixtures, pH 6 at 25° C. Modified Method The solubility method a included a 5-minute period between subsequent additions of solvent, to allow dissolution. Due to the increased viscosity in vehicles containing PEGs, the rate of dissolution is reduced. This was performed to investigate whether the rate of dissolution itself could cause the reduction in solubility of FC observed in PEG-vehicles. The solubility of FC decreased from 49 mg/ml with 2.5% PEG300 to about 25 mg/ml with 30% PEG300. The corresponding figures for the 5-minute method was 19 mg/ml and 8 mg/ml, respectively.

It was expected that the solubility would generally be higher with this modified method. More important, the course of the curve was almost identical to the original solubility curve thereby indicating that the reducing effect of PEGs on solubility is most likely caused by the solvent itself and not by the analytical method.

Calculation of Doses

Assuming a delivery volume of 100 μl, a dose of 1 mg fentanyl base, equivalent to approximately 1.6 mg fentanyl citrate, requires a formulation concentration of about 16 mg/ml. At room temperature, the corresponding PEG-concentration is about 5% w/w Conclusion From the data generated it can be concluded that PEG200 and PEG300 decreases the solubility of FC in water and in buffer at pH 6. Without pH-control, PEGs increase pH. The solubility of FC is lower in PEG300 than in PEG200 and reduction of temperature clearly decreases the solubility of FC. In conclusion, nasal formulations of FC delivering 1 mg fentanyl in 100 μl volumes can be achieved using PEG-concentrations up to 2.5% w/w.

Example 6

Effect of Periods

Data for the two days of surgery were compared for all PK-variables. Significant differences were found for $AUC_{0-3}$, $C_{max}$, HVD (PP population) and $MRT_{0-3}$ (PP population) Also SPID differed for the first and second day of surgery. $AUC_{0-3}$ and $C_{max}$ were both lower in the first period compared to the second. For $AUC_{0-3}$: 5% lower for nasal, 14% lower for i.v.; for $C_{max}$: 5% for nasal, 42% lower for i.v. In the PP population this period effect was more pronounced, probably due to fewer patients. For variables with significant period effect, this was taken into account when statistical analyses were performed, i.e. when comparing formulations and doses.

Primary Endpoint $AUC_{0-3}$ $AUC_{0-3-nasal}$ increased from 34.9 ng×min/ml for 75 μg to 81.9 ng×min/ml for 200 μg fentanyl. For i.v. administration the corresponding figures were 28.0 and 88.3 ng×min/ml. Linear dose-$AUC_{0-3}$ relationships were found for both routes of administration and both populations When routes of administration were compared, i.e. the four doses pooled, $AUC_{0-3\ nasal}$ was higher than $AUC_{0-3-i.v.}$ with bioavailabilities of 107% and 110% for the exploratory and PP-populations, respectively. The differences between $AUC_{0-3-nasal}$ and $AUC_{0-3-i.v.}$ were not significant (p=0.14 and p=0.085)

Secondary Endpoints $AUC_{0-\infty}$ $AUC_{0-\infty-nasal}$ increased from 67.7 ng×min/ml for 75 μg to 138.6 ng×min/ml for 200 μg fentanyl. For i.v. administration the corresponding figures were 47.0 and 137.3 ng×min/ml (exploratory population). Linear dose-$AUC_{0-\infty}$ relationships were found for both routes of administration and both populations.

When routes of administration were compared, i.e. results for the four doses pooled, $AUC_{0-\infty-nasal}$ was higher than $AUC_{0-\infty-i.v.}$ with bioavailabilities of 116% and 119% for the exploratory and PP-populations, respectively. The difference between $AUC_{0-3-nasal}$ and $AUC_{0-\infty-i.v}$ was significant for the PP but not for the exploratory population (p=0.045 and p=0.071).

$C_{max}$ $C_{max-nasal}$ in the exploratory population increased from 0.7 ng/ml for 75 μg to 1.7 ng/ml for 200 μg fentanyl. The corresponding results for the i.v. formulation were 0.9 and 2.6 ng/ml. Linear dose-concentration relationships were found for i.v. administration in both populations and for nasal administration in the exploratory population.

When routes of administration were compared, i.e. results for the four doses pooled, peak concentration of nasal versus i.v. fentanyl was 71% for the exploratory population (p=0.016). For the PP population this figure was 67% (p=0.013).

$T_{max}$

When routes of administration were compared, i.e. results for the four doses pooled, mean $T_{max}$ was 12.8 min for nasal and 6.0 min for i.v. administration. The corresponding values for the PP population were 13.0 and 5.8 min (p<<0.0001 for both populations.

$MRT_{0-3}$ $MRT_{0-3}$ varied between 61.8 and 69.7 min There was no dose-$MRT_{0-3}$ relationship for either population. $MRT_{0-3}$ nasal tended to be higher than $MRT_{0-3-i.v.}$ for the PP population (p=0.054) but this was not the case for the exploratory population (p=0.17).

$MRT_{0-\infty}$ $MRT_{0-\infty}$ varied between 125.6 and 257.4 min. There was no dose relationship and no difference between the two formulations.

HVD $HVD_{nasal}$ varied between 19.0 and 46.4 min whereas results for i.v. administration were between 10.6 and 30.3 min. No dose relationships were seen (p=0.34 exploratory, p=0.17 PP). HVD was 15.2 min in the i.v. PP group, i.e. 13 min shorter than in the nasal group (p=0.0002). For the exploratory population this difference was 8 min (p=0.12).

$T_{>75\%}$ Cmax $T_{>75\% \, Cmax}$ varied between 8.2 and 16.6 min after nasal administration and between 3.4 and 7.7 min after i.v. administration. There was no dose relationship (p=0.20). $T_{>75\% \, Cmax}$ was 6 min shorter after i.v. than after nasal administration (p=0.0005). For the PP-population the dose relationship was significant and linear for the nasal formulation (p=0.045) whereas there was no dose relationship for the i.v. formulation (p=0.81). $T_{>75\% \, Cmax}$ was 7 min shorter after i.v. than after nasal administration (p=0.001) in the PP population.

$K_e$ $K_e$ varied between 0.0052 and 0.0073 after nasal administration and between 0.0047 and 0.0076 after i.v. administration. No differences between routes of administration or doses were observed for either population.

Pain Intensity—PI

For all eight treatment groups the nadir of pain appeared at 15 or 30 min. For the smaller doses, the lowest value generally was recorded once; for the higher doses up to three times.

Sum of Pain Intensity Difference—SPID

No significant differences between administration routes were found for either population or between doses. The high standard deviations of $SPID_{0-4}$ are explained by the calculation method after intake of rescue medication. When this took place, i.e. approx. 1 hour after intake of fentanyl, the highest pain intensity score (either baseline or last value before rescue medication) was maintained until 4 hours. In order to reduce standard deviations, SPID for 60 min was calculated. No significant differences were, however, found after reducing the period of observation to 60 min Time to Onset of Analgesic Effect Median time to onset of effect was 1 min for i.v. and 7 min for nasal administration with the four doses pooled (p=0.0001). No dose-response relationship was found (p=0.75 and 0.55) For the exploratory population median time to onset was 2 min for i.v. and 7 min for nasal administration (p=0.0001).

The results are illustrated in FIG. 5

Duration of Analgesic Effect

Median duration of effect was 49 min for i.v. and 56 min for nasal administration with the four doses pooled (p=0.61) A trend towards significant dose-response relationship for nasal administration was seen (p=0.098). For the exploratory population the dose-response relationship was significant with a median duration of 47 min for 75 µg and 89 min for 200 µg (p=0.04)

The mean scores for pain intensity at onset and offset of analgesic effect were at time points 1.7 and 2.3 for onset, 4.1 and 4.7 for offset of effect after i.v. and nasal administration, respectively.

Rescue Medication

The amount of analgesic rescue medication, i.e. ibuprofen 600 mg and any other analgesics, is summarised below.

During the first 4 hours after surgery, ibuprofen was taken in all cases but one. The mean dose was 1.1 ibuprofen tablet. The patients received a total of 10 ibuprofen tablets for supplementary analgesic treatment during the week after tooth extraction. The mean intake was 8.2 tablets. Other analgesics were taken as well. Paracetamol was the analgesic most frequently taken.

The numbers of ibuprofen tablets taken per dose and route during the week after surgery was 1.8 tablets less after nasal (mean intake) than after i.v. administration (doses pooled) (p<0.005).

Time to Rescue Medication

Median time to rescue medication was 63 min for i.v. and 68 min for nasal administration (p=0.87). For the nasal route dose-response was close to significance in both populations (p=0.081 and 0.051, respectively).

General Impression

Scores for general impression increased with dose, i.e. satisfaction with test treatment was more pronounced with the higher doses. Scores tended to be higher for i.v. than for nasal administration.

Efficacy Conclusions

Pharmacokinetic Variables

Presentation of pharmacokinetic variables is based on the exploratory population. Linear dose-AUC relationships were found for both routes of administration. When nasal and i.v. administrations were compared, differences of $AUC_{0-3}$ and $AUC_{0-\infty}$, were not significant. The bioavailability of the nasal formulation therefore was interpreted to be 100%.

A linear relationship between dose and $C_{max}$ was found for both routes of administration. With the four doses pooled, peak concentration of nasal versus i.v. fentanyl was 71% whereas mean $T_{max}$ was 12.8 min for nasal and 6.0 min for i.v. administration.

Pharmacodynamic Variables

Presentation of pharmacodynamic variables is based on the PP population. As reflected in SPID, no significant differences in analgesia between administration routes were found for either population or between doses.

Median time to onset of meaningful effect was 1 min for i.v. and 7 min for nasal administration with the four doses pooled. No dose-response relationships were found. For the exploratory population the median time to onset was 2 min for i.v. and 7 min for nasal administration. The i.v. formulation as seen resulted in a faster onset of pain reduction. This difference was not reflected in the Pain Intensity profiles since pain was recorded only at 15 and 30 min after administration.

Median duration of effect was 49 min for i.v. and 56 min for nasal administration. For the exploratory population the dose-response relationship was significant with a median duration of 47 min for 75 µg and 89 min for 200 µg.

That median time to rescue medication was 63 min for i.v. and 68 min for nasal administration supports the impression that analgesic effect is comparable for the two routes of administration.

Scores for general impression increased with dose, i.e. satisfaction with test treatment was more pronounced with the higher doses. Scores tended to be higher for i.v. than for nasal administration.

Example 7

Adverse Events

No serious adverse events were recorded in this trial.

The percentages of patients reporting adverse events seem fairly equally distributed across the three lower doses whereas the number of events was high in the 200 µg dose group. Vertigo was the most frequently reported most of which were in connection to intravenous administration. Respiratory depression was recorded 6 times, 5 of which in relation to intravenous administration. Adverse events were coded according to the WHO Adverse Reaction Dictionary version 1999.

In intravenous administration, adverse events such as pain or inflammation at the site of injection are obviously not observed for intravenous administration. At 150 µg administered intravenously, respiratory depression was observed 3 times whereas at said dose, respiratory depression was not observed for intranasal administration.

Tolerability. Nasal

Nasal tolerability, i.e. sore, itching or stinging nose, sore or stinging throat, dry or stuffy nose, runny nose and taste disturbance was identical for nasal and intravenous administration.

Tolerability. CNS Effects. Sedation and Nausea

Findings for the two CNS tolerability variables sedation and nausea indicated that sedation was seen after all but two molar extractions. Worsening of nausea was recorded in 3 patients receiving nasal and 6 patients receiving i.v. fentanyl. Nausea scores were higher in the 150 and 200 µg dose groups. Conclusions were similar for cut off time points 60 and 240 min.

Tolerability. Mental State

For the questions: Are you feeling "high"? Is your speech less loud than usually? Are your surroundings more pleasant than usually? about one fourth of the patients answered Yes. There seemed to be no differences between formulations. There was a tendency towards dose response relationship for feeling high. Only a few patients responded to the question Do you feel more like in a dream than awake?

There were no deaths or serious/significant adverse events.

Example 8

Oxygen Saturation

Oxygen saturation was the only laboratory variable tested. There seemed to be no difference between routes of administration but a tendency towards lower oxygen saturation that lasted longer with increasing fentanyl doses.

Baseline values ranged from 94 to 100%. Only one patient had 94% as baseline and this value was the lowest recorded for this patient. Excluding this patient, baseline values ranged from 96 to 100%. The lowest value for individual patients seen during the 240 min period varied between 92 and 98%. These low values were seen only once in the respective patients who received 150/200 µg i.v., 200 µg i.v. and 100/150/200 µg nasal doses, respectively. The last oxygen saturation values at 240 min varied between 96 and 100%.

Oxygen Saturation

There seemed to be no difference between routes of administration but a tendency towards lower oxygen saturation that lasted longer with increasing fentanyl doses. This is quite in line with expectations. It may be concluded that for this group of healthy patients, oxygen saturation remained satisfactory during the treatment period.

Discussion

Trial Model, Design and GCP Compliance

The pain model—removal of an impacted mandibular third molar—is a standardised model for investigation of analgesic potency of opioids and other analgesics. The model is well documented. It has the benefit of being suitable for use in both sides of the lower jaw allowing a cross-over design and thereby minimising the variance in pharmacokinetic and pharmacodynamic responses. The single dose design used reflects the therapeutic explanatory nature of this trial. Randomisation and double-blind administration of test treatment was used to avoid bias. For ethical reasons a placebo group was not included. I.v. fentanyl was chosen as comparator since bioavailability of the fentanyl formulations were to be compared.

Using a university clinic specialised in running this model further had the advantage that it was used to handle, inform and treat patients in a uniform way. The staff has profound experience in data collection and ICH-GCP requirements from a substantial number of trials with this model.

Discussion of Data Obtained

The use of fentanyl should be monitored by clinical assessment. The use of plasma concentrations of fentanyl may be clinically useful; however, plasma levels do not reflect patient sensitivity to fentanyl and therefore should not be used as a sole determinant of efficacy or toxicity.

Fentanyl Concentration Levels

In opioid-naive patients analgesia has been obtained in the range 0.2 to 1.2 ng/mL (16), confirming that this study reached therapeutic analgesic plasma concentrations of fentanyl.

$C_{max-nasal}$ in the exploratory population increased from 0.7 ng/ml for 75 µg to 1.7 ng/ml for 200 µg fentanyl. The corresponding results for the i.v. formulation were 0.9 and 2.6 ng/ml. Linear dose-concentration relationships were found for i.v. administration in both populations and for nasal administration in the exploratory population. The smaller $C_{max-nasal}$ may hint a more favourable side effect profile for nasally administered fentanyl in regard to side effects related to plasmaconcentration.

Mean $T_{max}$ in the exploratory population was 12.8 min for nasal and 6.0 min for i.v. administration. The corresponding values for the PP population were 13.0 and 5.8 min. It is reported in literature that time to peak concentrations after a standardized consumption time of 15 minutes for doses of 200, 400, 800, and 1600 micrograms oral transmucosal fentanyl produced peak concentrations after 20 to 40 minutes (16). Further when 3 doses of oral transmucosal fentanyl citrate 800 micrograms were given 6 hours apart to 12 healthy volunteers, median times to peak concentration were 24, 22, and 23.5 minutes for the respective doses. The $T_{max-nasal}$ is therefor seen as satisfactory in regard to the comparable alternative fentanyl treatments. The nasally administered fentanyl in this trial reached recognised therapeutic drug level and demonstrated a shorter time to peak concentration than for Actiq.

Bioavailability

When routes of administration are compared, the differences between $AUC_{0-3-nasal}$ and $AUC_{0-3-i.v.}$ respectively $AUC_{0-\infty-nasal}$ and $AUC_{0-\infty-i.v.}$ are not significant. The bioavailability of the nasal formulation is therefor interpreted to be 100%. Some concern has been given to the period effect. It has not been possible to elucidate the apparent difference between periods in regard to administration of fentanyl or otherwise.

In publications the bioavailability of other nasal formulations in different delivery systems has been demonstrated to be around 70%. A different device delivering different sized drops in a maybe less precise manner can explain the very low bioavailability in regard to the one obtained in this study. Further, other studies administer doses several time introducing possibility for loss at every dose. Another aspect is the capability of fentanyl to adhere to sudden surfaces. It is not clear whether this fact is is taken into account in the published studies.

Oral transmucosal formulations is reported to have a bioavailability of 50% (16).

Onset of Effect

In obtaining analgesia a quick onset of effect is important. Median time to onset in the present trial was 1 min after i.v. and 7 min after nasal administration. In real life situations it takes time before an i.v. injection can be prepared and given by a nurse or doctor whereas nasal administration can be handled by the patients themselves immediately after the need of analgesia is recognised. Thus the fastest pain relief may well be obtained after nasal self administration of fentanyl.

In the present trial fentanyl was given to "healthy" patients. It is, however, believed that PK and analgetic variables will be similar in other, e.g. cancer, patients. Onset of effect after nasal administration was at least as good as results found after i.m. (7-8 min (16)) and p.o. transmucosal administration (within 15 min, (16))

Duration of Effect

Duration of analgesic effect here was found to be 49 min after i.v. and 56 min after nasal administration. Duration of analgesia after a single i.v. dose (up to 100 µg) has been found to be 30-60 min (16). After i.m. administration duration may be 1-2 hours (16).

A recent publication elucidated break-through pain (BTP) in hospice patients in which 72% of the BTP epsodes lasted less than 30 min (16) In these patients morphine tablets with a duration of several hours may cause side effects, e.g. nausea and mental incapacity, for a much longer period than the pain relief obtained with the tablet was needed. In these patients fentanyl by nasal administration may give the required pain relief without causing prolonged side effects. The effect of nasal fentanyl in BTP in cancer patients has recently been demonstrated (15).

The variety of diseases and conditions causing acute pain allows no simple assumption as to optimal duration of analgesia. Numerous clinical conditions, however, exist in which self administered efficient pain relief obtained quickly—as with nasal fentanyl—may be valuable. Nasal fentanyl may be given either alone or as supplementary pain therapy. Examples are pain in connection with postoperative mobilization, short-lasting procedures like change of dressings, angina pectoris, gall stones and trauma. For episodes requiring pain relief for a longer period than supplied by a single dose of fentanyl, nasal administration may be repeated.

The analgesic properties of the two formulations were presented as pain intensity, pain intensity difference and sum of pain intensity difference. Results indicated that total analgesia obtained with the two formulations did not differ.

Scores for general impression increased with dose, i.e. satisfaction with test treatment was more pronounced with the higher doses. Scores tended to be higher for i.v. than for nasal administration. The higher scores for i.v. may reflect the fact that both medications are received when doses are received.

Safety

Safety conclusions based on single dose exposure have only limited value because steady-state plasma concentrations and possible accumulation of drug will not occur. Thus, the full adverse event profile of fentanyl was not investigated here. In future trials, special attention should be given to the risk of respiratory depression since hypoventilation may occur throughout the therapeutic range of fentanyl. The risk, however, increases with plasma levels above 2 ng/ml in non-opioid tolerant patients, especially patients with an underlying pulmonary condition or who receive other drugs causing respiratory depression (16). Significant respiratory depression has developed with plasma fentanyl concentrations 1-3 nl/ml whereas respiratory effects were insignificant below 0.7 nl/ml. There is no predictable relationship between plasma fentanyl concentrations and $P_{CO2}$ (16). In opioid-naïve patients an increase in CNS effects occurred with plasma fentanyl levels above 3 ng/ml (16).

The adverse event profile for fentanyl, however, was consistent with the adverse events expected for this compound.

Benefits of Nasal Administration

Nasal administration of fentanyl offers a range of benefits. It is ideal for patients with nausea or vomiting, obstipation or impaired gastro-intestinal absorption. The ease of administration will facilitate compliance in less motivated patients like children and mentally confused/disabled patients.

Nasal fentanyl can be taken by the patients themselves allowing the comfort of independence from the medical staff. The psychological aspect of being independent and knowing that efficient analgesia can be obtained quickly may even reduce the need for medication. Nasal administration is non-invasive and therefore may minimize the risk of infections. Nasal fentanyl may also be a cost efficient alternative in patient controlled analgesia.

Indications

The main indications of nasal fentanyl appear to be BTP in cancer patients, bedside therapy in postoperative pain, benign acute pain episodes like angina pectoris, gall stones, trauma and change of dressing. Also pediatric patients may benefit from the easy administration of nasal fentanyl. A broad range of organisations dealing with emergency/acute pain situations, e.g. military, fleet, airlines, rescue teams and sport management, may find the efficiency, quick onset and easy use of fentanyl interesting.

The pharmacokinetic results compared well with the pharmacokinetic characteristics known for fentanyl. The bioavailability of nasal fentanyl did not differ from that of i.v. fentanyl.

An onset of analgesic effect within minutes as seen in this trial is an important benefit in treating pain. The limited duration of action of nasal fentanyl of approximately 1 hour may also be a benefit in numerous clinical scenarios.

The analgesic properties of the two formulations were presented as pain intensity, pain intensity difference and sum of pain intensity difference. Results indicated that total analgesia obtained with the two formulations did not differ. These observations and the benefits of the nasal route of administration make nasal fentanyl a most promising new way of treating pain either used alone or as supplementary pain therapy.

REFERENCES

1. World Medical Association Declaration of Helsinki. Recommendations guiding physicians in biomedical research involving human subjects
2. MICROMEDEX Healthcare Series NEW Integrated Index™, Drugdex Drug Evaluation: Fentanyl, latest update 06/98, Internet version
3. Shannon C N, Baranowski A P. Use of opioids in non-cancer pain. Br J Hosp Med 1997; 58: 459-463

4. Schwagmeier R, Oelmann T, Dannappel T, Striebel H W. Patient acceptance of patient-controlled intranasal analgesia (PCINA). Anaesthesist 1996; 45: 231-234
5. Striebel H W, Koenigs D, Kramer J. Postoperative pain management by intranasal demand-adapted fentanyl titration. Anesthesiology 1992; 77: 281-285
6. Striebel H W, Kramer J, Luhmann 1, Rohierse-Hohler I, Rieger A. Pharmakokinetische Studie zur intranasalen Gabe von Fentanyl. Der Schmertz 1993; 7: 122-125
7. O'Neil G, Paech M, Wood F. Preliminary clinical use of a patient-controlled intranasal analgesia (PCINA) device. Anaesth Intensive Care 1997; 25: 408412
8. Personal communication from Høgskilde S. Safety and efficacy experience from fentanyl usage at 'Leageambulancen'. April 2000
9. Taburet A M, Steimer J L, Doucet D, Singlas E. Le temps de présence moyen dans l'organisme. Un nouveau paramètre pharmacocinétique? Therapie 1986; 41: 1-10
10. Yamaoka K, Nakagawa T, Uno T. Statistical moments in pharmacokinetics. J Pharmacokin Biopharm 1978; 6: 547-58
11. Meier J, Nüesch E, Schmidt R. Pharmacokinetic criteria for the evaluation of retard formulations. Eur J Clin Pharmacol 1974; 7: 429-32
12. Striebel H W, et al. Intranasal fentanyl titration for postoperative pain management in an unselected population. Anaesthesia 1993; 48: 753-7.
13. Striebel H W, et al. Patient-controlled intranasal analgesia: a method for noninvasive postoperative pain management. Anesth Analg 1996; 83: 548-51.6228/a5/80-g.
14. Zeppetella G. An assessment of the safety, efficacy, and acceptability of intranasal fentanyl citrate in the management of cancer related breakthrough pain: a pilot study. J Pain Symptom Manage 2000; 20(4):253-258
15. Zeppetella G. Nebulized and intranasal fentanyl in the management of cancerrelated breakthrough pain. Palliat Med 2000; 14(1):57-58
16. MicroMedex Healthcare Services 2001; Volume 108

TABLE 1

75 µg Fentanyl subject no.

| Nominal Time (min) | 1 Concentration (ng/ml) | | 2 Concentration (ng/ml) | | 3 Concentration (ng/ml) | |
|---|---|---|---|---|---|---|
| | Nasal | i.v. | Nasal | i.v. | Nasal | i.v. |
| 0 | <0.02 | <0.02 | <0.02 | <0.02 | <0.02 | <0.02 |
| 1 | <0.02 | 0.0223 | <0.02 | 0.665 | <0.02 | 0.165 |
| 3 | 0.0322 | 1.58 | 0.107 | 1.21 | 0.0290 | 1.10 |
| 5 | 0.366 | 0.826 | 0.253 | 0.756 | 0.343 | 0.758 |
| 7 | 0.592 | 0.756 | 0.359 | 0.673 | 0.686 | 0.596 |
| 9 | 0.692 | 0.479 | 0.297 | 0.527 | 0.758 | 0.537 |
| 12 | 0.564 | 0.311 | 0.767 | 0.368 | 0.658 | 0.392 |
| 15 | 0.483 | 0.321 | 0.699 | 0.248 | 0.528 | 0.364 |
| 25 | 0.298 | 0.255 | 0.388 | 0.251 | 0.408 | 0.238 |
| 40 | 0.157 | 0.189 | 0.251 | 0.234 | 0.247 | 0.140 |
| 60 | 0.136 | 0.154 | 0.215 | 0.187 | 0.158 | 0.113 |
| 90 | 0.113 | 0.131 | 0.165 | 0.132 | 0.154 | 0.0781 |
| 120 | 0.0882 | 0.111 | 0.162 | 0.122 | 0.120 | 0.0728 |
| 180 | 0.0796 | 0.106 | 0.174 | 0.109 | 0.0564 | 0.0436 |

TABLE 2

100 µg Fentanyl

| 4 Concentration (ng/ml) | | 5 Concentration (ng/ml) | | 6 Concentration (ng/ml) | | 7 Concentration (ng/ml) | |
|---|---|---|---|---|---|---|---|
| Nasal | i.v. | Nasal | i.v. | Nasal | i.v. | Nasal | i.v. |
| <0.02 | <0.02 | <0.02 | <0.02 | <0.02 | <0.02 | <0.02 | <0.02 |
| <0.02 | 1.25 | <0.02 | 0.284 | <0.02 | 0.162 | <0.02 | 0.0753 |
| <0.02 | 2.69 | <0.02 | 3.35 | 0.138 | 2.79 | <0.02 | 1.52 |
| 0.0566 | 1.64 | 0.0838 | 1.36 | 0.588 | 1.27 | 0.0566 | 1.01 |
| 0.361 | 1.22 | 0.255 | 1.42 | 0.948 | 1.20 | 0.120 | 0.952 |
| 0.565 | 1.10 | 0.520 | 1.07 | 1.12 | 0.938 | 0.643 | 0.798 |
| 1.01 | 0.776 | 0.912 | 0.735 | 0.872 | 0.755 | 0.897 | 0.519 |
| 0.914 | 0.649 | 0.661 | 0.609 | 0.622 | 0.618 | 0.584 | 0.453 |
| 0.689 | 0.385 | 0.365 | 0.479 | 0.437 | 0.390 | 0.428 | 0.281 |
| 0.462 | 0.312 | 0.358 | 0.389 | 0.336 | 0.308 | 0.303 | 0.200 |
| 0.308 | 0.297 | 0.297 | 0.321 | 0.300 | 0.346 | 0.218 | 0.161 |
| 0.326 | 0.205 | 0.217 | 0.189 | 0.214 | 0.268 | 0.183 | 0.133 |
| 0.273 | 0.176 | 0.208 | 0.173 | 0.206 | 0.191 | 0.142 | 0.133 |
| 0.132 | 0.112 | 0.208 | 0.197 | 0.185 | 0.186 | 0.0836 | 0.0698 |

TABLE 3

| | 150 μg Fentanyl Subject No. | | | | | | |
|---|---|---|---|---|---|---|---|
| | 8 Concentration (ng/ml) | | 9 Concentration (ng/ml) | | 10 Concentration (ng/ml) | | |
| Nominal Time (min) | Nasal | i.v. | Nasal | i.v. | Nasal | i.v. | i.v. |
| 0 | <0.02 | <0.02 | <0.02 | <0.02 | <0.02 | <0.02 | <0.02 |
| 1 | <0.02 | <0.02 | <0.02 | 0.0822 | <0.02 | 5.35 | 0.186 |
| 3 | 0.119 | 0.0422 | <0.02 | 0.976 | 0.0522 | 2.12 | 0.738 |
| 5 | NS | 0.370 | <0.02 | 0.688 | 0.566 | 1.28 | 1.03 |
| 7 | 0.261 | 5.07 | 0.0587 | 2.96 | 1.54 | 4.07 | 4.13 |
| 9 | 1.33 | 2.67 | 0.175 | 1.50 | 2.39 | 2.06 | 2.08 |
| 12 | 1.41 | 1.19 | 0.464 | 0.823 | 2.28 | 1.44 | 1.59 |
| 15 | 1.58 | 0.771 | 1.06 | 0.714 | 1.64 | 0.964 | 1.14 |
| 25 | 1.12 | 0.751 | 0.866 | 0.547 | 1.03 | 0.640 | 0.893 |
| 40 | 0.78 | 0.530 | 0.857 | 0.464 | 0.627 | 0.597 | 0.626 |
| 60 | 0.559 | 0.489 | 0.610 | 0.407 | 0.44 | 0.548 | 0.538 |
| 90 | 0.418 | 0.325 | 0.383 | 0.359 | 0.373 | 0.380 | 0.371 |
| 120 | 0.267 | 0.211 | 0.278 | 0.278 | 0.333 | 0.303 | 0.407 |
| 180 | 0.182 | 0.170 | 0.202 | 0.177 | 0.264 | 0.242 | 0.257 |

TABLE 4

| 200 μg Fentanyl | | | | |
|---|---|---|---|---|
| 11 Concentration (ng/ml) | | 12 Concentration (ng/ml) | | 13 Concentration (ng/ml) |
| Nasal | i.v. | Nasal | i.v. | Nasal |
| <0.02 | <0.02 | <0.02 | <0.02 | <0.02 |
| <0.02 | 0.0291 | <0.02 | 0.602 | <0.02 |
| <0.02 | 0.352 | <0.02 | 1.96 | <0.02 |
| <0.02 | 0.802 | 0.0220 | 1.32 | 0.0399 |
| 0.0622 | 2.43 | 0.148 | 4.62 | 0.101 |
| 0.233 | 1.33 | 0.930 | 2.23 | 0.595 |
| 0.802 | 0.853 | 3.23 | 1.41 | 1.10 |
| 0.961 | 0.657 | 3.10 | 1.03 | 1.52 |
| 0.761 | 0.479 | 1.52 | 0.788 | 0.854 |
| 0.535 | 0.409 | 0.819 | 0.828 | 0.588 |
| 0.367 | 0.374 | 0.590 | 0.432 | 0.542 |
| 0.302 | 0.334 | 0.478 | 0.302 | 0.409 |
| 0.292 | 0.297 | 0.343 | 0.381 | 0.193 |
| 0.269 | 0.188 | 0.263 | 0.215 | 0.167 |

TABLE 5

| | 75 μg Fentanyl Subject No. | | | | | | | | | | | |
|---|---|---|---|---|---|---|---|---|---|---|---|---|
| | 1 | | | | 2 | | | | 3 | | | |
| Nominal Time (min) | Nasal | | i.v. | | Nasal | | i.v. | | Nasal | | i.v. | |
| | PI | PID | PI | PID | PI | PID | PI | PID | PI | PID | PI | PID |
| 0 | 5 | 0 | 3 | 0 | 8 | 0 | 4 | 0 | 6 | 0 | 3 | 0 |
| 15 | 1 | 4 | 0 | 2 | 5 | 3 | 2 | 2 | 1 | 5 | 0 | 3 |
| 30 | 3 | 2 | 0 | 0 | 6 | 2 | 4 | 0 | 4 | 2 | 0 | 3 |
| 45 | 4 | 1 | 2 | 0 | 8 | 0 | 4 | 0 | 6 | 0 | 2 | 1 |
| 60 | 5 | 0 | 3 | 0 | 8 | 0 | 4 | 0 | 6 | 0 | 3 | 0 |
| 75 | 5 | 0 | 3 | 0 | 8 | 0 | 4 | 0 | 6 | 0 | 3 | 0 |
| 90 | 5 | 0 | 3 | 0 | 8 | 0 | 4 | 0 | 6 | 0 | 3 | 0 |
| 105 | 5 | 0 | 3 | 0 | 8 | 0 | 4 | 0 | 6 | 0 | 3 | 0 |
| 120 | 5 | 0 | 3 | 0 | 8 | 0 | 4 | 0 | 6 | 0 | 3 | 0 |
| 150 | 5 | 0 | 3 | 0 | 8 | 0 | 4 | 0 | 6 | 0 | 3 | 0 |
| 180 | 5 | 0 | 3 | 0 | 8 | 0 | 4 | 0 | 6 | 0 | 3 | 0 |
| 210 | 5 | 0 | 3 | 0 | 8 | 0 | 4 | 0 | 6 | 0 | 3 | 0 |
| 240 | 5 | 0 | 3 | 0 | 8 | 0 | 4 | 0 | 6 | 0 | 3 | 0 |

TABLE 6

| 100 μg Fentanyl | | | | | | | | | | | | | | | |
|---|---|---|---|---|---|---|---|---|---|---|---|---|---|---|---|
| 4 | | | | 5 | | | | 6 | | | | 7 | | | |
| Nasal | | i.v. | | Nasal | | i.v. | | Nasal | | i.v. | | Nasal | | i.v. | |
| PI | PID | PI | PID | PI | PID | PI | PID | PI | PID | PI | PID | PI | PID | PI | PID |
| 7 | 0 | 3 | 0 | 5 | 0 | 3 | 0 | 5 | 0 | 4 | 0 | 3 | 0 | 6 | 0 |
| 1 | 6 | 1 | 2 | 1 | 4 | 1 | 2 | 1 | 4 | 1 | 3 | 0 | 3 | 1 | 5 |
| 2 | 5 | 6 | −3 | 3 | 2 | 2 | 1 | 2 | 3 | 3 | 1 | 3 | 0 | 6 | 0 |
| 3 | 4 | 6 | −3 | 4 | 1 | 3 | 0 | 4 | 1 | 4 | 0 | 3 | 0 | 6 | 0 |
| 5 | 2 | 6 | −3 | 5 | 0 | 3 | 0 | 5 | 0 | 4 | 0 | 3 | 0 | 6 | 0 |
| 7 | 0 | 6 | −3 | 5 | 0 | 3 | 0 | 5 | 0 | 4 | 0 | 3 | 0 | 6 | 0 |
| 7 | 0 | 6 | −3 | 5 | 0 | 3 | 0 | 5 | 0 | 4 | 0 | 3 | 0 | 6 | 0 |
| 7 | 0 | 6 | −3 | 5 | 0 | 3 | 0 | 5 | 0 | 4 | 0 | 3 | 0 | 6 | 0 |
| 7 | 0 | 6 | −3 | 5 | 0 | 3 | 0 | 5 | 0 | 4 | 0 | 3 | 0 | 6 | 0 |
| 7 | 0 | 6 | −3 | 5 | 0 | 3 | 0 | 5 | 0 | 4 | 0 | 3 | 0 | 6 | 0 |
| 7 | 0 | 6 | −3 | 5 | 0 | 3 | 0 | 5 | 0 | 4 | 0 | 3 | 0 | 6 | 0 |
| 7 | 0 | 6 | −3 | 5 | 0 | 3 | 0 | 5 | 0 | 4 | 0 | 3 | 0 | 6 | 0 |
| 7 | 0 | 6 | −3 | 5 | 0 | 3 | 0 | 5 | 0 | 4 | 0 | 3 | 0 | 6 | 0 |

TABLE 7

| | 150 μg Fentanyl Subject No. | | | | | | | | | | | | |
|---|---|---|---|---|---|---|---|---|---|---|---|---|---|
| Nominal | 8 | | | | 9 | | | | 10 | | | | |
| Time | Nasal | | i.v. | | Nasal | | i.v. | | Nasal | | i.v. | | |
| (min) | PI | PID | PI | PID | PI | PID | PI | PID | PI | PID | PI | PID |
| 0 | 5 | 0 | 2 | 0 | 5 | 0 | 4 | 0 | 4 | 0 | 5 | 0 |
| 15 | 0 | 5 | 0 | 2 | 1 | 4 | 0 | 4 | 1 | 3 | 0 | 5 |
| 30 | 0 | 5 | 0 | 2 | 1 | 4 | 2 | 2 | 0 | 4 | 0 | 5 |
| 45 | 0 | 5 | 1 | 1 | 5 | 0 | 4 | 0 | 1 | 3 | 1 | 4 |
| 60 | 2 | 3 | 2 | 0 | 6 | −1 | 4 | 0 | 2 | 2 | 3 | 2 |
| 75 | 3 | 2 | 2 | 0 | 6 | −1 | 4 | 0 | 4 | 0 | 5 | 0 |
| 90 | 3 | 2 | 2 | 0 | 6 | −1 | 4 | 0 | 4 | 0 | 5 | 0 |
| 105 | 4 | 1 | 2 | 0 | 6 | −1 | 4 | 0 | 4 | 0 | 5 | 0 |
| 120 | 5 | 0 | 2 | 0 | 6 | −1 | 4 | 0 | 4 | 0 | 5 | 0 |
| 150 | 5 | 0 | 2 | 0 | 6 | −1 | 4 | 0 | 4 | 0 | 5 | 0 |
| 180 | 5 | 0 | 2 | 0 | 6 | −1 | 4 | 0 | 4 | 0 | 5 | 0 |
| 210 | 5 | 0 | 2 | 0 | 6 | −1 | 4 | 0 | 4 | 0 | 5 | 0 |
| 240 | 5 | 0 | 2 | 0 | 6 | −1 | 4 | 0 | 4 | 0 | 5 | 0 |

TABLE 8

| 200 μg Fentanyl | | | | | | | | | | | |
|---|---|---|---|---|---|---|---|---|---|---|---|
| 11 | | | | 12 | | | | 13 | | | |
| Nasal | | i.v. | | Nasal | | i.v. | | Nasal | | i.v. | |
| PI | PID | PI | PID | PI | PID | PI | PID | PI | PID | PI | PID |
| 2 | 0 | 6 | 0 | 5 | 0 | 6 | 0 | 5 | 0 | 3 | 0 |
| 0 | 2 | 1 | 5 | 1 | 4 | 1 | 5 | 0 | 5 | 0 | 3 |
| 0 | 2 | 1 | 5 | 1 | 4 | 2 | 4 | 0 | 5 | 0 | 3 |
| 1 | 1 | 2 | 4 | 3 | 2 | 4 | 2 | 0 | 5 | 1 | 2 |
| 3 | −1 | 4 | 2 | 5 | 0 | 8 | −2 | 1 | 4 | 4 | −1 |
| 4 | −2 | 4 | 2 | 5 | 0 | 8 | −2 | 4 | 1 | 4 | −1 |
| 4 | −2 | 6 | 0 | 5 | 0 | 8 | −2 | 5 | 0 | 4 | −1 |
| 4 | −2 | 6 | 0 | 5 | 0 | 8 | −2 | 5 | 0 | 4 | −1 |
| 4 | −2 | 6 | 0 | 5 | 0 | 8 | −2 | 5 | 0 | 4 | −1 |
| 4 | −2 | 6 | 0 | 5 | 0 | 8 | −2 | 5 | 0 | 4 | −1 |
| 4 | −2 | 6 | 0 | 5 | 0 | 8 | −2 | 5 | 0 | 4 | −1 |
| 4 | −2 | 6 | 0 | 5 | 0 | 8 | −2 | 5 | 0 | 4 | −1 |

The invention claimed is:

1. A method for the treatment of pain in a mammal, which comprises intranasally administering, by a nasal spray to the nasal mucosal membrane of said mammal, at least a single dosage unit having a volume of 10 to 200 μl in one administration by one delivery operation comprising a fentanyl salt in an amount equivalent to 70 to 500 μg of fentanyl in a solvent comprising water, to deliver a treatment dosage of from 70 to 1000 μg of fentanyl until a time-to-onset-of-action, said dosage unit being in the form of a composition having a concentration equivalent to about 0.4 to 75 mg/ml of fentanyl.

2. The method according to claim 1, wherein said administration comprises the delivery of at least a single dosage unit equivalent to 75 to 300 μg of fentanyl.

3. The method according to claim 1, wherein said administration comprises the delivery of at least a single dosage unit equivalent to 75 μg fentanyl.

4. The method according to claim 1 wherein the mammal is a human.

5. The method according to claim 1 wherein said administration comprises the delivery of at least a single dosage unit equivalent to 100 μg fentanyl.

6. The method according to claim 1 wherein said administration comprises the delivery of at least a single dosage unit equivalent to 150 µg of fentanyl.

7. The method according to claim 1 wherein said administration comprises the delivery of at least a single dosage unit equivalent to 200 µg of fentanyl.

8. The method according to claim 1, wherein said fentanyl salt is fentanyl citrate.

9. The method according to claim 1, wherein said solvent further comprises isotonic saline, polyethylene glycol, or a combination thereof.

10. The method according to claim 1, wherein said solvent comprises about 95%-100% water.

11. The method according to claim 9 wherein said single dosage unit consists essentially of fentanyl salt and said solvent.

12. The method according to claim 1 wherein the treatment is alleviation or lessening of acute or breakthrough pain.

13. The method according to claim 1 wherein the mammal further receives an analgesic.

14. The method according to claim 13, wherein the analgesic is fentanyl, or a salt thereof.

15. The method according to claim 12 wherein said acute or breakthrough pain comprises colic/biliary pain, trauma, post-operative pain, dental pain, orofacial pain, sympathetic pain syndrome, pancreatic pain, myocardial infarction pain, cancer pain, back pain, or pain during or after change of dressing.

16. The method according to claim 1 wherein said method is for pre-operative anesthesia.

17. The method according to claim 1 wherein said administration comprises the delivery of at least a single dosage unit equivalent to 400 µg of fentanyl.

18. The method of claim 17 wherein the treatment is alleviation or lessening of breakthrough pain.

19. The method according to claim 1, wherein the volume of the single dosage unit is 50 to 150 µl.

20. The method according to claim 1, wherein the single dosage unit is in the form of a composition having a concentration equivalent to about 0.5 to 20 mg/ml of fentanyl.

21. The method according to claim 1, wherein the single dosage unit is in the form of a composition having a concentration equivalent to about 0.6 to 15 mg/ml of fentanyl.

22. The method according to claim 1, wherein the single dosage unit is in the form of a composition having a concentration equivalent to about 0.7 to 12 mg/ml of fentanyl.

23. The method according to claim 1, wherein the single dosage unit is in the form of a composition having a concentration equivalent to about 0.75 to 10 mg/ml of fentanyl.

24. The method according to claim 1, wherein the single dosage unit is in the form of a composition having a concentration equivalent to about 0.75 to 8 mg/ml of fentanyl.

* * * * *